(12) United States Patent
Holgate et al.

(10) Patent No.: US 11,059,903 B2
(45) Date of Patent: Jul. 13, 2021

(54) ANTI-PSMA ANTIBODIES, USES THEREOF AND CONJUGATES THEREOF

(71) Applicant: Polytherics Limited, Cambridge (GB)

(72) Inventors: Robert George Edward Holgate, Royston (GB); Arron Robert Hearn, Ely (GB)

(73) Assignee: POLYTHERICS LIMITED, Cambridge (GB)

( * ) Notice: Subject to any disclaimer, the term of this patent is extended or adjusted under 35 U.S.C. 154(b) by 0 days.

(21) Appl. No.: 16/303,600

(22) PCT Filed: Aug. 18, 2017

(86) PCT No.: PCT/GB2017/052448
§ 371 (c)(1),
(2) Date: Nov. 20, 2018

(87) PCT Pub. No.: WO2018/033749
PCT Pub. Date: Feb. 22, 2018

(65) Prior Publication Data
US 2019/0300623 A1 Oct. 3, 2019

(30) Foreign Application Priority Data

Aug. 18, 2016 (GB) ...................................... 1614162

(51) Int. Cl.
| | | |
|---|---|---|
| A61K 39/00 | (2006.01) | |
| C07K 16/30 | (2006.01) | |
| A61K 47/68 | (2017.01) | |
| A61P 35/00 | (2006.01) | |

(52) U.S. Cl.
CPC ...... *C07K 16/3069* (2013.01); *A61K 47/6803* (2017.08); *A61K 47/6869* (2017.08); *A61P 35/00* (2018.01); *C07K 2317/24* (2013.01); *C07K 2317/73* (2013.01); *C07K 2317/92* (2013.01); *C07K 2317/94* (2013.01)

(58) Field of Classification Search
CPC . A61K 47/6869; A61K 47/6803; A61P 35/00; A61P 13/08; C07K 2317/24
See application file for complete search history.

(56) References Cited

U.S. PATENT DOCUMENTS

| | | | |
|---|---|---|---|
| 8,470,330 B2 | 6/2013 | Maddon | |
| 10,780,120 B2* | 9/2020 | Zhao | A61P 35/00 |
| 2004/0136998 A1 | 7/2004 | Bander | |
| 2020/0345778 A1* | 11/2020 | Zhao | C07K 14/70521 |

FOREIGN PATENT DOCUMENTS

| | | |
|---|---|---|
| WO | 1998/03873 | 1/1998 |
| WO | 2003/034903 | 5/2003 |
| WO | 2004/098535 | 11/2004 |
| WO | 2006/089230 | 8/2006 |
| WO | 2009/017823 | 2/2009 |
| WO | 2015/057250 | 4/2015 |
| WO | 2015/177360 | 11/2015 |
| WO | 2016/063006 | 4/2016 |

OTHER PUBLICATIONS

Paul, Fundamental Immunology, 3rd Edition, 1993, pp. 292-295 (Year: 1993).*
Rudikoff et al(Proc. Natl. Acad. Sci. USA 1982 vol. 79: p. 1979). (Year: 1979).*
Pascalis et al (The Journal of Immunology (2002) 169, 3076-3084) (Year: 2002).*
Casset et al. (2003) BBRC 307, 198-205, (Year: 2003).*
Kataja et al., Ann Oncol 2009; 20(sup 4): iv10-14 (Year: 2009).*
Nelson et al., Ann. Intern Med. 2009; 151:727-737 (Year: 2009).*
Balmana et al. Ann Oncol 2009; 20(supp 4):iv19-20 (Year: 2009).*
Nakajima, et al., (2011) "Targeted, Activatable, In Vivo Fluorescence Imaging of Prostate-Specific Membrane Antigen (PSMA) Positive Tumors Using the Quenched Humanized J591 Antibody-Indocyanine Green (ICG) Conjugate", Bioconjugate Chemistry, 22(8):1700-1705.
Murga, et al., (2014) "Synergistic co-targeting of prostate-specific membrane antigen and androgen receptor in prostate cancer", Prostate., 75(3):242-254.
Wang, et al., (2011) "In Vitro and In Vivo Responses of Advanced Prostate Tumors to PSMA ADC, an Auristatin-conjugated Antibody to Prostate-Specific Membrane Antigen", Molecular Cancer Therapeutics, 10 (9):1728-1739.
Tagawa, et al., (2010) "Anti-Prostate-Specific Membrane Antigen-Based Radioimmunotherapy for Prostate Cancer", Cancer, 116(4)1075-1083.

* cited by examiner

*Primary Examiner* — Sheela J. Huff
(74) *Attorney, Agent, or Firm* — Carol L. Francis; Bozicevic, Field & Francis LLP

(57) ABSTRACT

An antibody or antigen-binding portion thereof which binds to PSMA and comprises a heavy chain variable domain comprising the sequences: CDR1: EYTIH (SEQ ID NO: 33) CDR2: NINPNX$^1$GGTTYNQKFED (SEQ ID NO: 34) CDR3: X$^{2-5}$DY (SEQ ID NO: 35) wherein X$^1$ is N or Q, and X$^{2-5}$ is YWLF (SEQ ID NO: 39), GWTF (SEQ ID NO: 40) or AWTM (SEQ ID NO: 41), and wherein if X$^{2-5}$ is GWTF (SEQ ID NO: 40) or AWTM (SEQ ID NO: 41), the amino acid residue at position H94 in the heavy chain variable region, based on Kabat numbering, is G; and if X$^{2-5}$ is YWLF (SEQ ID NO: 39), the amino acid residue at position H94 in the heavy chain variable region, based on Kabat numbering, is A. The invention also provides compounds that include the antibody or antigen-binding portion thereof, such as conjugates, and their use in the treatment or diagnosis of disease, in particular cancers, particularly prostate cancer.

31 Claims, 11 Drawing Sheets

Specification includes a Sequence Listing.

Amino Acid Sequences

Murine J591 VH Amino Acid>Seq ID 1
EVQLQQSGPELKKPGTSVRISCKTSGYTFTEYTIHWVKQSHGKSLEWIGNINPNNGGT
TYNQKFEDKATLTVDKSSSTAYMELRSLTSEDSAVYYCAAGWNFDYWGQGTTLTV
SS Murine J591 Vκ Amino Acid>Seq ID 2
DIVMTQSHKFMSTSVGDRVSIICKASQDVGTAVDWYQQKPGQSPKLLIYWASTRHT
GVPDRFTGSGSGTDFTLTITNVQSEDLADYFCQQYNSYPLTFGAGTMLDLK AB-10 Deimmunised J591 VH Amino Acid>Seq ID 3
EVQLVQSGPEVKKPGATVKISCKTSGYTFTEYTIHWVKQAPGKGLEWIGNINPNNGG
TTYNQKFEDKATLTVDKSTDTAYMELSSLRSEDTAVYYCAAGWNFDYWGQGTLLT
VSS AB-10 Deimmunised J591 Vκ Amino Acid>Seq ID 4
DIQMTQSPSSLSTSVGDRVTLTCKASQDVGTAVDWYQQKPGPSPKLLIYWASTRHT
GIPSRFSGSGSGTDFTLTISSLQPEDFADYYCQQYNSYPLTFGPGTKVDIK AB-02 and AB-05 VH Amino Acid>Seq ID 5
EVQLVQSGAEVKKPGASVKVSCKASGYTFTEYTIHWVRQAPGKGLEWIGNINPNNG
GTTYNQKFEDRVTITVDKSTSTAYMELSSLRSEDTAVYYCAAYWLFDYWGQGTTVT
VSS AB-01 and AB-02 Vκ Amino Acid>Seq ID 6
DIQMTQSPSTLSASVGDRVTITCKASQDVGTAVDWYQQKPGQAPKLLIYWASTRHT
GVPDRFSGSGSGTDFTLTISRLQPEDFAVYYCQQYNSYPLTFGQGTKVDIK

*FIG. 3*

AB-03 VH Amino Acid>Seq ID 7
EVQLVQSGAEVKKPGASVKVSCKASGYTFTEYTIHWVRQAPGKGLEWIGNINPNNG
GTTYNQKFEDRVTITVDKSTSTAYMELSSLRSEDTAVYYCAGGWTFDYWGQGTTVT
VSS AB-03 and AB-04 Vκ Amino Acid>Seq ID 8
DIQMTQSPSTLSASVGDRVTITCKASQDVGTAVDWYQQKPGQAPKLLIYWASTRHT
GVPDRFSGSGSGTDFTLTISRLQPEDFAVYYCQQFTRYPLTFGQGTKVDIK AB-04 VH Amino Acid>Seq ID 9
EVQLVQSGAEVKKPGASVKVSCKASGYTFTEYTIHWVRQAPGKGLEWIGNINPNNG
GTTYNQKFEDRVTITVDKSTSTAYMELSSLRSEDTAVYYCAGAWTMDYWGQGTTV
TVSS AB-05, AB-06 and AB-07 Vκ Amino Acid>Seq ID 10
DIQMTQSPSTLSASVGDRVTITCKASQDVGTAVDWYQQKPGQAPKLLIYWASTRHT
GVPDRFSGSGSGTDFTLTISRLQPEDFAVYYCQQYNAYSLTFGQGTKVDIK AB-06 VH Amino Acid>Seq ID 11
EVQLVQSGAEVKKPGASVKVSCKASGYTFTEYTIHWVRQAPGKGLEWIGNINPNNG
GTTYNQKFEDRVTITVDKSTSTAYMELSSPRSEDTAVYYCAAGWNFDYWGQGTTVT
VSS AB-01 and AB-07 VH Amino Acid>Seq ID 12
EVQLVQSGAEVKKPGASVKVSCKASGYTFTEYTIHWVRQAPGKGLEWIGNINPNNG
GTTYNQKFEDRVTITVDKSTSTAYMELSSLRSEDTAVYYCAAGWNFDYWGQGTTV
TVSS

FIG. 3 Cont'd

AB-08 VH Amino Acid>Seq ID 13

MELGLRWGFL VALLRGVQCQ VQLVESGGGV VQPGRSLRLS CAASGFAFSR
YGMHWVRQAP GKGLEWVAVI WYDGSNKYYA DSVKGRFTIS RDNSKNTQYL
QMNSLRAEDT AVYYCARGGD FLYYYYYGMD VWGQGTTVTV SS

This is the sequence presented as SEQ ID NO 15 in US 8,470,332 B

AB-08 VK Amino Acid>Seq ID 14

MRVPAQLLGL LLLWLPDTRC DIQMTQSPSS LSASVGDRVT ITCRASQGIS
NYLAWYQQKT GKVPKFLIYE ASTLQSGVPS RFSGGGSGTD FTLTISSLQP
EDVATYYCQN YNSAPFTFGP GTKVDIK

This is the sequence presented as SEQ ID NO 17 in US 8,470,332 B

AB-09 VH Amino Acid>Seq ID 15

MELGLRWVLL VALLRGVQCQ VQLVESGGGV VQPGRSLRLS CAASGFTFSN
YVMHWVRQAP GKGLEWVAII WYDGSNKYYA DSVKGRFTIS RDNSKNTLYL
QMNSLRAEDT AVYYCAGGYN WNYEYHYYGM DVWGQGTTVT VSS

This is the sequence presented as SEQ ID NO 19 in US 8,470,332 B

AB-09 VK Amino Acid>Seq ID 16

MRVPAQLLGL LLLCFPGARC DIQMTQSPSS LSASVGDRVT ITCRASQGIT
NYLAWFQQKP GKAPKSLIYA ASSLQSGVPS KFSGSGSGTD FSLTISSLQP
EDFATYYCQQ YNSYPITFGQ GTRLEIK

This is the sequence presented as SEQ ID NO 21 in US 8,470,332 B

FIG. 3 Cont'd

DNA Sequences

Murine J591 VH DNA>Seq ID 17
GAGGTCCAGCTGCAACAGTCTGGACCTGAGCTGAAGAAGCCTGGGACTTCAGTG
AGGATATCCTGCAAGACTTCTGGATACACATTCACTGAATACACCATCCACTGGG
TGAAGCAGAGCCATGGAAAGAGCCTTGAGTGGATTGGAAACATTAATCCTAACA
ATGGTGGTACTACCTACAACCAGAAGTTCGAGGACAAGGCCACATTGACTGTAG
ACAAGTCCTCCAGCACAGCCTACATGGAGCTCCGCAGCCTGACATCTGAGGATTC
TGCAGTCTATTACTGTGCAGCTGGTTGGAACTTTGACTACTGGGGCCAAGGCACC
ACGCTCACCGTCTCCTCA Murine J591 Vκ DNA>Seq ID 18
GACATTGTGATGACCCAGTCTCACAAATTCATGTCCACATCAGTAGGAGACAGG
GTCAGCATCATCTGCAAGGCCAGTCAGGATGTGGGTACTGCTGTAGACTGGTATC
AACAGAAACCAGGGCAATCTCCTAAACTACTGATTTACTGGGCATCCACCCGGC
ACACTGGAGTCCCTGATCGCTTCACAGGCAGTGGATCTGGGACAGATTTCACTCT
CACCATCACCAATGTGCAGTCTGAAGACCTGGCAGATTATTTCTGTCAGCAATAT
AACAGCTATCCTCTCACGTTCGGCGCCGGGACCATGCTGGATCTCAAA AB-10 Deimmunised J591 VH DNA>Seq ID 19
GAGGTCCAACTGGTACAGTCTGGACCTGAAGTGAAGAAGCCTGGGGCTACAGTG
AAGATATCCTGCAAGACTTCTGGATACACATTCACTGAATATACCATACACTGGG
TGAAGCAGGCCCCTGGAAAGGGCCTTGAGTGGATTGGAAACATCAATCCTAACA
ATGGTGGTACCACCTACAATCAGAAGTTCGAGGACAAGGCCACACTAACTGTAG
ACAAGTCCACCGATACAGCCTACATGGAGCTCAGCAGCCTAAGATCTGAGGATA
CTGCAGTCTATTATTGTGCAGCTGGTTGGAACTTTGACTACTGGGGCCAAGGGAC
CCTGCTCACCGTCTCCTCA

FIG. 4

AB-10 Deimmunised J591Vκ DNA>Seq ID 20
GACATCCAGATGACCCAGTCTCCCTCATCCCTGTCCACATCAGTAGGAGACAGGG
TCACCCTCACCTGTAAGGCCAGTCAAGATGTGGGTACTGCTGTAGACTGGTATCA
ACAGAAACCAGGACCATCTCCTAAACTACTGATTTATTGGGCATCCACTCGGCAC
ACTGGAATCCCTAGTCGCTTCTCAGGCAGTGGATCTGGGACAGACTTCACTCTCA
CCATTTCTAGTCTTCAGCCTGAAGACTTTGCAGATTATTACTGTCAGCAATATAAC
AGCTATCCTCTCACGTTCGGTCCTGGGACCAAGGTGGACATCAAA AB-02 and AB-05 VH DNA>Seq ID 21
GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGTCACAATCACTGTAG
ACAAGTCCACCAGCACAGCCTACATGGAGCTCAGCAGCCTGAGATCTGAGGATA
CTGCAGTCTATTACTGTGCAGCTTACTGGCTGTTCGACTACTGGGGCCAAGGCAC
CACGGTCACCGTCTCCTCA AB-01 and AB-02 Vκ DNA>Seq ID 22
GACATTCAGATGACCCAGTCTCCCAGCACCCTGTCCGCATCAGTAGGAGACAGG
GTCACCATCACTTGCAAGGCCAGTCAGGATGTGGGTACTGCTGTAGACTGGTATC
AACAGAAACCAGGGCAAGCTCCTAAACTACTGATTTACTGGGCATCCACCCGGC
ACACTGGAGTCCCTGATCGCTTCAGCGGCAGTGGATCTGGGACAGATTTCACTCT
CACCATCAGCAGACTGCAGCCTGAAGACTTTGCAGTTTATTACTGTCAGCAATAT
AACAGCTATCCTCTCACGTTCGGCCAGGGGACCAAGGTGGATATCAAA

FIG. 4 Cont'd

AB-03 VH DNA>Seq ID 23

GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGTCACAATCACTGTAG
ACAAGTCCACCAGCACAGCCTACATGGAGCTCAGCAGCCTGAGATCTGAGGATA
CTGCAGTCTATTACTGTGCAGGTGGGTGGACCTTCGACTACTGGGGCCAAGGCAC
CACGGTCACCGTCTCCTCA

AB-03 and AB-04 Vκ DNA>Seq ID 24

GACATTCAGATGACCCAGTCTCCCAGCACCCTGTCCGCATCAGTAGGAGACAGG
GTCACCATCACTTGCAAGGCCAGTCAGGATGTGGGTACTGCTGTAGACTGGTATC
AACAGAAACCAGGGCAAGCTCCTAAACTACTGATTTACTGGGCATCCACCCGGC
ACACTGGAGTCCCTGATCGCTTCAGCGGCAGTGGATCTGGGACAGATTTCACTCT
CACCATCAGCAGACTGCAGCCTGAAGACTTTGCAGTTTATTACTGTCAGCAGTTC
ACCAGGTATCCTCTCACGTTCGGCCAGGGGACCAAGGTGGATATCAAA

AB-04 VH DNA>Seq ID 25

GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGTCACAATCACTGTAG
ACAAGTCCACCAGCACAGCCTACATGGAGCTCAGCAGCCTGAGATCTGAGGATA
CTGCAGTCTATTACTGTGCAGGTGCGTGGACCATGGACTACTGGGGCCAAGGCAC
CACGGTCACCGTCTCCTCA

FIG. 4 Cont'd

AB-05, AB-06 and AB-07 Vκ DNA>Seq ID 26
GACATTCAGATGACCCAGTCTCCCAGCACCCTGTCCGCATCAGTAGGAGACAGG
GTCACCATCACTTGCAAGGCCAGTCAGGATGTGGGTACTGCTGTAGACTGGTATC
AACAGAAACCAGGGCAAGCTCCTAAACTACTGATTTACTGGGCATCCACCCGGC
ACACTGGAGTCCCTGATCGCTTCAGCGGCAGTGGATCTGGGACAGATTTCACTCT
CACCATCAGCAGACTGCAGCCTGAAGACTTTGCAGTTTATTACTGTCAGCAATAT
AACGCGTACTCGTTGACGTTCGGCCAGGGGACCAAGGTGGATATCAAA AB-06 VH DNA>Seq ID 27
GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGTCACAATCACTGTAG
ACAAGTCCACCAGCACAGCCTACATGGAGCTCAGCAGCCCGAGATCTGAGGATA
CTGCAGTCTATTACTGTGCAGCTGGTTGGAACTTTGACTACTGGGGCCAAGGCAC
CACGGTCACCGTCTCCTCA AB-01 and AB-07 VH DNA>Seq ID 28
GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGTCACAATCACTGTAG
ACAAGTCCACCAGCACAGCCTACATGGAGCTCAGCAGCCTGAGATCTGAGGATA
CTGCAGTCTATTACTGTGCAGCTGGTTGGAACTTTGACTACTGGGGCCAAGGCAC
CACGGTCACCGTCTCCTCA

FIG. 4 Cont'd

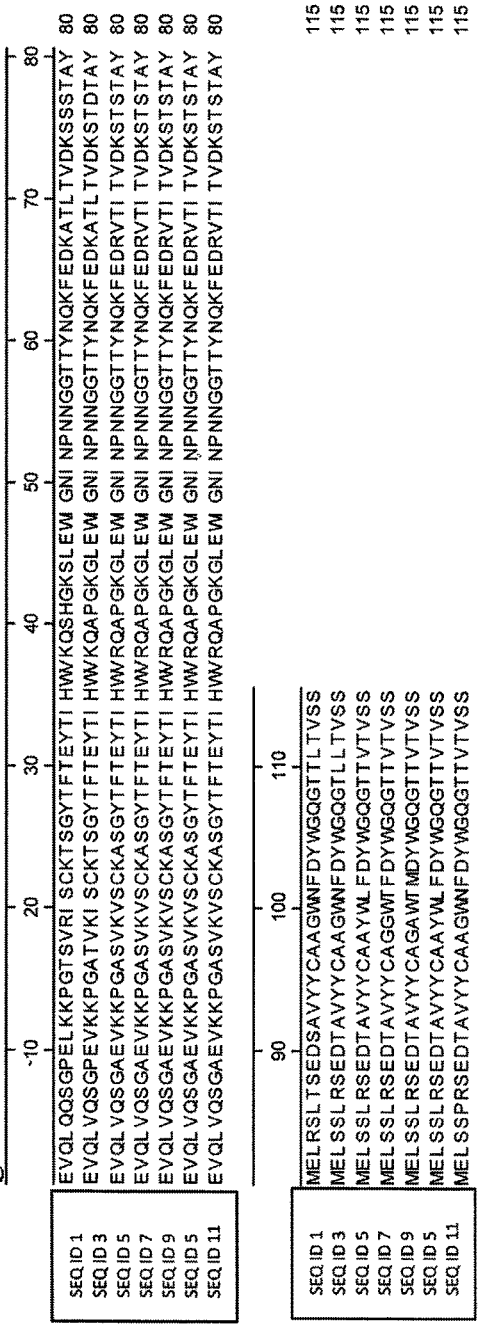
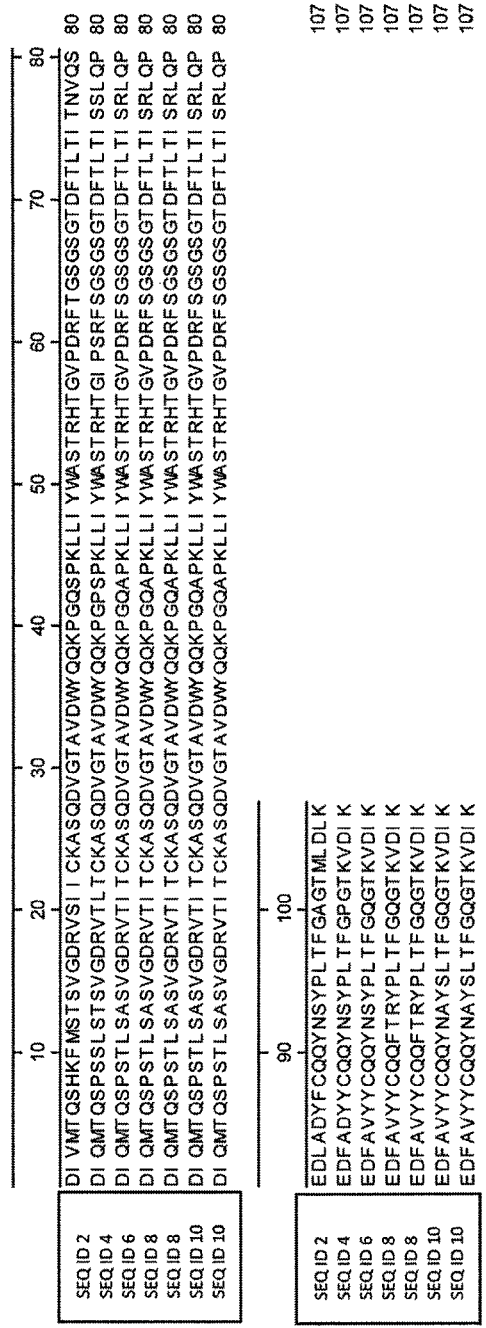
FIG. 5

ANTI-PSMA ANTIBODIES, USES THEREOF AND CONJUGATES THEREOF

The present invention relates to novel humanised antibodies that bind to PSMA, uses of the antibodies and compounds that include the antibodies, for example conjugates of the antibodies, for example antibody-drug conjugates. The antibodies and conjugates of the invention find use in the treatment or diagnosis of diseases, in particular cancers, particularly prostate cancer.

BACKGROUND TO THE INVENTION

The specificity of antibodies for specific antigens on the surface of target cells and molecules has led to their extensive use as carriers of a variety of diagnostic and therapeutic agents. For example, antibodies conjugated to labels and reporter groups such as fluorophores, radioisotopes and enzymes find use in labelling and imaging applications, while conjugation to cytotoxic agents and chemotherapy drugs allows targeted delivery of such agents to specific tissues or structures, for example particular cell types or growth factors, minimising the impact on normal, healthy tissue and significantly reducing the side effects associated with chemotherapy treatments. Antibody-drug conjugates have extensive potential therapeutic applications in several disease areas.

Prostate cancer, also known as carcinoma of the prostate, is the development of cancer in the prostate, a gland in the male reproductive system. Globally it is the second most common type of cancer and the fifth leading cause of cancer-related death in men. First line therapy for advanced prostate cancer is androgen deprivation. Following progression, chemotherapy offers benefit, but responses are transient and there is no therapy that has been shown to improve survival beyond initial chemotherapy. Metastatic prostate cancer is poorly responsive to conventional chemotherapy. There thus remains a need for improved therapies.

Prostate Specific Membrane Antigen (PSMA) expression is highly associated with prostate cancer and with other solid tumours. PSMA is present on the cell surface of some normal prostatic epithelial cells, normal renal proximal tubular cells, proximal small bowel and some astrocytes (found in the brain). PSMA is highly upregulated/overexpressed on prostate cancer (PCa) cells. Expression levels of PSMA increase along with prostate cancer progression and high PSMA levels in early stage prostate cancer predict an increased likelihood of recurrence. A significant proportion of solid tumours express PSMA in their tumor neo-vasculature whereas normal vascular endothelium is PSMA-negative. It has been observed that PSMA increases available folates by hydrolyzing glutamated folates. It has been postulated that PSMA stimulates the development of prostate cancer by increasing folate levels for the cancer cells to use to survive and grow.

Anti-PSMA antibodies have previously been generated (see for example WO98/03973) and modified antibodies with reduced immunogenicity in humans have been prepared (see for example WO2004/098535). An example of a de-immunised IgG monoclonal antibody that binds PSMA is J591. The amino acid sequence of the variable domain heavy chain of the murine J591 antibody is given herein as SEQ ID NO:1, and the corresponding light chain is given herein as SEQ ID NO:2. The amino acid sequence of the variable domain heavy chain of the de-immunised antibody J591 is given herein as SEQ ID NO: 3, and the corresponding light chain is given herein as SEQ ID NO:4. De-immunised J591 has been used in radiolabelled form in the clinic and it has been shown to be well-tolerated and non-immunogenic (see Tagawa et al., *Cancer,* 2010, 116(4), 1075-1083).

Further examples of antibodies that bind PSMA are disclosed in WO03/034903 and its family members, including U.S. Pat. No. 8,470,330B. For example, antibody "AB-PG1-XG1-006" has heavy and light chain sequences SEQ ID NO 15 and SEQ ID NO 17 in those publications (given herein as SEQ ID NO's 13 and 14), and antibody "AB-PG1-XG1-026" has heavy and light chain sequences SEQ ID NO 19 and SEQ ID NO 21 in those publications (given herein as SEQ ID NO's 15 and 16).

In addition to having good target binding affinity, low off-target binding and low immunogenicity, an antibody that is to be a candidate as a drug (whether on its own or conjugated to another active component) should have good stability. That is to say it should have a low propensity to denature or aggregate, or disassociate into component fragments. Given this set of demanding properties, there remains a need for the development of further beneficial anti-PSMA antibodies.

SUMMARY OF THE INVENTION

The present invention relates to novel humanised antibodies which bind to PSMA. The invention provides an antibody or antigen-binding portion thereof which binds to PSMA and comprises a heavy chain variable domain comprising the sequences:

```
                                            (SEQ ID NO: 33)
     CDR1: EYTIH (SEQ ID NO: 34)
     CDR2: NINPNX¹GGTTYNQKFED (SEQ ID NO: 35)
     CDR3: X²⁻⁵DY
``` wherein
$X^1$ is N or Q, and
$X^{2-5}$ is YWLF (SEQ ID NO: 39), GWTF (SEQ ID NO: 40) or AWTM (SEQ ID NO: 41),
and wherein
if $X^{2-5}$ is GWTF (SEQ ID NO: 40) or AWTM (SEQ ID NO: 41), the amino acid residue at position H94 in the heavy chain variable region, based on Kabat numbering, is G; and if $X^{2-5}$ is YWLF (SEQ ID NO: 39), the amino acid residue at position H94 in the heavy chain variable region, based on Kabat numbering, is A.

Preferably, $X^1$ is N.

The CDRs of the heavy chain may be designated as CDRH1, CDRH2 and CDRH3, respectively. According to the Kabat numbering system (Kabat et al., 1991, Sequences of Proteins of Immunological Interest, 5th Ed., United States Public Health Service, National Institutes of Health, Bethesda), CDRH1 is located from position H31 to H35, CDRH2 is from H50 to H65 and CDRH3 is from H95 to H102.

In preferred embodiments, the antibody or antigen-binding portion thereof of the Invention comprises a heavy chain variable domain comprising the sequence given in SEQ ID NO: 29, wherein

```
SEQ ID NO: 29 is:
EVQLVQSGAE VKKPGASVKV SCKASGYTFT EYTIHWVRQA

PGKGLEWIGN INPNNGGTTY NQKFEDRVTI TVDKSTSTAY

MELSSLRSED TAVYYCAX⁹⁸X⁹⁹⁻¹⁰²DYWGQGTT VTVSS
``` wherein:
$X^{98-102}$ is AYWLF (SEQ ID NO: 42), GGWTF (SEQ ID NO: 43), or GAWTM (SEQ ID NO: 44), whereby the heavy chain variable domain comprises up to 12 amino acid sequence modification(s) at any of positions 1-30, 36-49, 67-97 and 104-115 of SEQ ID NO: 29.

In preferred embodiments, the antibody or antigen-binding portion thereof of the Invention comprises a heavy chain variable domain comprising the sequence given in SEQ ID NO: 30, wherein SEQ ID NO: 30 is:
EVQLVQSGX$^9$E X$^{11}$KKPGASVKV SCKX$^{24}$SGYTFT EYTIHWVX$^{38}$QA

X$^{41}$GKGLEWIGN INPNX$^{55}$GGTTY NQKFEDRX$^{68}$TX$^{70}$ TVDKSTSTAY

MELSSX$^{86}$RSED TAVYYCAX$^{98}$X$^{99}$X$^{100}$ X$^{101}$X$^{102}$DYWGQGTT

VTVSS wherein:
X$^9$ is A or P
X$^{11}$ is V or L
X$^{24}$ is A or T
X$^{38}$ is R or K
X$^{41}$ is P or H
X$^{55}$ is N or Q
X$^{68}$ is V or A
X$^{70}$ is I or L,
X$^{86}$ is L or P, and
X$^{98-102}$ is AYWLF (SEQ ID NO: 42), GGWTF (SEQ ID NO: 43), or GAWTM (SEQ ID NO: 44),
whereby the heavy chain variable domain comprises up to 3 amino acid sequence modification(s) between positions 1-30, 36-49, 67-98 and 105-115 of SEQ ID NO: 30, in addition to those specifically recited above.
X$^{98}$ in SEQ ID NOs: 29 and 30 corresponds to the amino acid residue at position H94 in the heavy chain variable region, based on Kabat numbering (Kabat et al., 1991, Sequences of Proteins of Immunological Interest, 5th Ed., United States Public Health Service, National Institutes of Health, Bethesda).

The present invention also provides an antibody or antigen-binding portion thereof which binds to PSMA and comprises a light chain variable domain comprising the sequences:

CDR1: KASQDVGTAVD (SEQ ID NO: 36)

CDR2: WASTRHT (SEQ ID NO: 37)

CDR3: QQX$^{1-5}$LT (SEQ ID NO: 38)

wherein X$^{1-5}$ is FTRYP (SEQ ID NO: 45) or YNAYS (SEQ ID NO: 46).

The CDRs of the light chain may be designated as CDRL1, CDRL2 and CDRL3, respectively. According to the Kabat numbering system, CDRL1 is located from position L24 to L34, CDRL2 is from L50 to L56 and CDRL3 is from L89 to L97.

In preferred embodiments, the antibody or antigen-binding portion thereof of the Invention comprises a light chain variable domain comprising the sequence given in SEQ ID NO: 31, wherein SEQ ID NO: 31 is:
DIQMTQSPST LSASVGDRVT ITCKASQDVG TAVDWYQQKP

GQAPKLLIYW ASTRHTGVPD RFSGSGSGTD FTLTISRLQP

EDFAVYYCQQ X$^{91-95}$LTFGQ GTKVDIK wherein
X$^{91-95}$ is FTRYP (SEQ ID NO: 45) or YNAYS (SEQ ID NO: 46),
whereby the light chain variable domain comprises up to 10 amino acid sequence modification(s) between positions 1-23, 35-49, 57-88 and 98-107 of SEQ ID NO: 31.

In other preferred embodiments, the antibody or antigen-binding portion thereof of the Invention comprises a light chain variable domain comprising the sequence given in SEQ ID NO: 32, wherein SEQ ID NO: 32 is:
DIX$^3$MTQSPSX$^{10}$ LSASVGDRVT ITCKASQDVG TAVDWYQQKP

GQAPKLLIYW ASTRHTGVPD RFX$^{63}$GSGSGTD FTLTISRLQX$^{80}$

EDFAX$^{85}$YX$^{87}$CQQ X$^{91-95}$LTFGQ GTX$^{103}$VDIK wherein
X$^3$ is Q or V
X$^{10}$ is T or F
X$^{63}$ is S or T
X$^{80}$ is P or S
X$^{85}$ is V or D
X$^{87}$ is Y or F
X$^{91-95}$ is FTRYP (SEQ ID NO: 45) or YNAYS (SEQ ID NO: 46); and
X$^{103}$ is K or M
whereby the light chain variable domain comprises up to 3 amino acid sequence modification(s) between positions 1-23, 35-49, 57-88 and 98-107 of SEQ ID NO: 32, in addition to those specifically recited above.

In preferred embodiments, the antibody or antigen-binding portion thereof comprises a heavy chain variable domain of the Invention and a light chain variable domain of the Invention.

The antibodies and antigen-binding portions of the Invention have strong binding to PSMA, in particular they have stronger binding than the deimmunised J591 antibody described above. Antibodies with high affinity for their antigen are advantageous as they can be used therapeutically in small quantities and they carry a lower risk of off-target effects.

In addition, preferred antibodies and antigen-binding portions of the Invention have good stability. Antibodies with good stability are advantageous as they have less propensity to denature or aggregate, or disassociate into component fragments. As a result, they may reside within the circulation in a native conformation for longer. Reduced fragmentation is an advantage as a fragmented antibody (or antibody-drug conjugate) loses its ability to bind to the target antigen. Cytotoxic drugs tend to be hydrophobic, and they thus show a tendency for aggregation in solution. A reduced tendency to aggregate is also an advantage for an antibody-drug conjugate. Aggregates can prompt an immune response, that is to say they can be immunogenic. An antibody-drug conjugate comprising an antibody or antigen-binding portion of the invention has good stability and a reduced tendency to aggregate in solution.

The antibodies and antigen-binding portions of the Invention also display good efficiency of expression. The efficiency of expression of the antibody is an important factor in production of an antibody or antibody-drug conjugate. For example, obtaining stable, high-yield expression of an antibody is important for production for diagnostic or therapeutic use, in which large quantities of an antibody are required even to conduct a clinical trial. The expression level of the light or heavy chains and their ease of manipulation throughout expression and purification may thus influence the choice of antibody selected for production. Antibodies that express well with high solubility and low propensity to aggregate are preferred.

BRIEF DESCRIPTION OF THE FIGURES

FIG. 3 shows the amino acid sequences of the antibodies exemplified herein.

FIG. 4 shows the DNA sequences utilised for the expression of the antibodies exemplified herein.

FIG. 5 shows the sequences of certain of the antibodies exemplified herein aligned with each other.

DETAILED DESCRIPTION

Figure 1A:
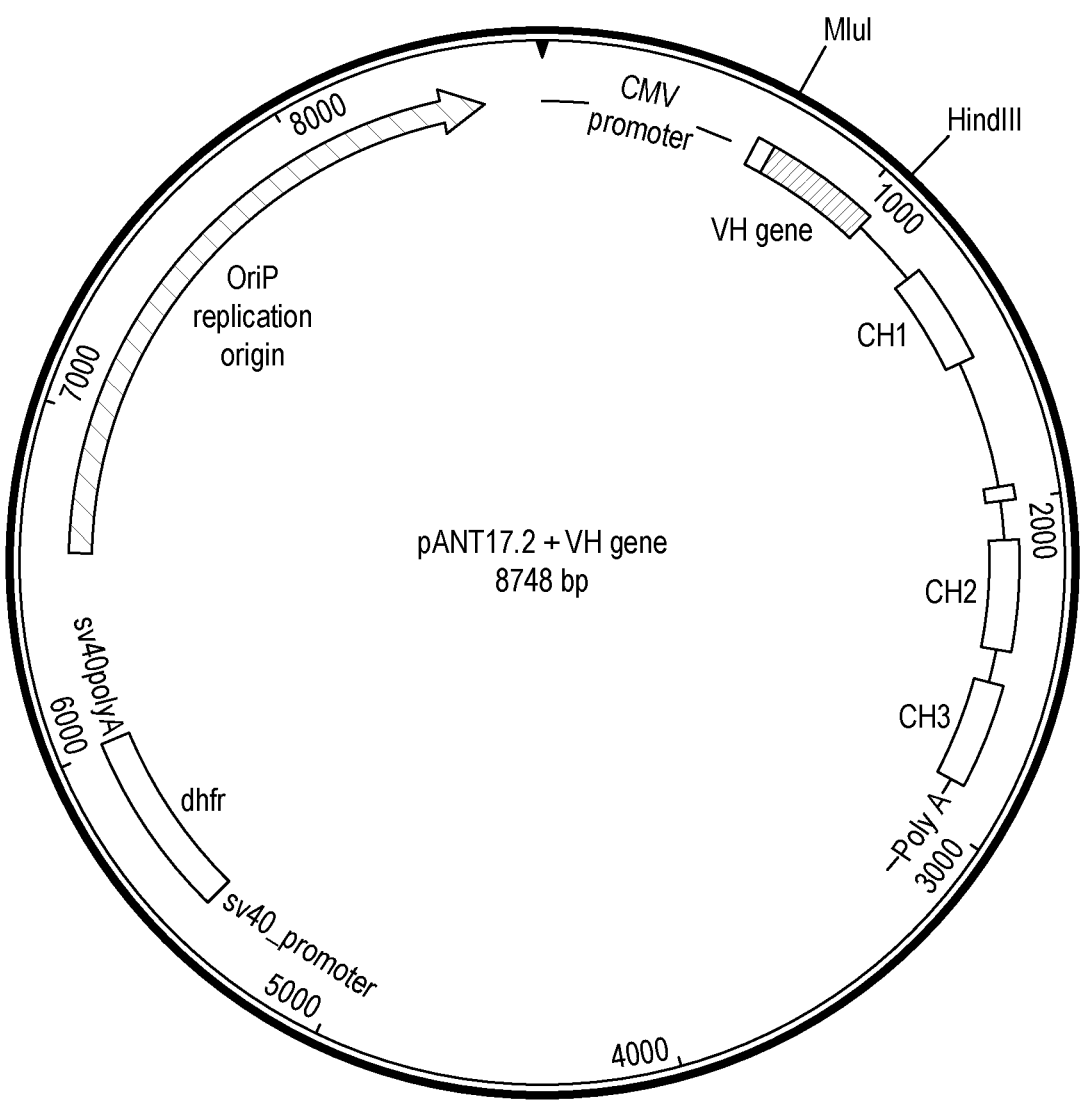
FIG. 1(a) shows the structure of the pANT expression vector for the heavy chain variable domain (pANT17.2).

The CDR regions are underlined in the Sequences SEQ ID NO: 29 to 32 above.

The present invention encompasses antibodies and antigen-binding portions thereof comprising a heavy chain variable domain comprising the sequence given in SEQ ID NO: 29, and having up to 12 amino acid sequence modification(s) outside the CDR regions as defined above, and/or a light chain variable domain comprising the sequence given in SEQ ID NO:31, and having up to 10 amino acid sequence modification(s) outside the CDR regions as defined above.

For example, such a modification may improve the binding affinity and/or other biological properties of an antibody. Amino acid sequence modification(s) can be prepared by introducing appropriate nucleotide changes into an antibody nucleic acid, or by peptide synthesis. Such modification(s) include, for example, deletions from, and/or insertions into and/or substitutions of, residues within the amino acid sequences of an antibody. Any combination of deletion, insertion, and substitution can be made to arrive at the final construct, provided that the final construct possesses the desired characteristics. Substitutions may be conservative or non-conservative substitutions. The amino acid changes also may alter post-translational processes of an antibody, such as changing the number or position of glycosylation sites.

For example, when the amino acid sequence modification is a substitution, it is preferably a conservative substitution, i.e., an amino acid substitution that does not substantially reduce specific binding (e.g., as measured by the $K_D$) of the antibody or antigen-binding portion thereof to an antigen (e.g., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

The present invention also encompasses antibodies and antigen-binding portions thereof comprising a heavy chain variable domain comprising the sequence given in SEQ ID NO:30, and/or a light chain variable domain comprising the sequence given in SEQ ID NO:32, and having an additional up to 3 amino acid sequence modification(s), for example 0, 1 or 2 amino acid sequence modification(s), outside the CDR regions as defined above, in one or both of the heavy chain and light chain variable domains.

The present invention also encompasses antibodies and antigen-binding portions thereof comprising a heavy chain variable domain comprising the sequence given in SEQ ID NO:29, and/or a light chain variable domain comprising the sequence given in SEQ ID NO:31, having up to 3 amino acid sequence modification(s), for example 0, 1 or 2 amino acid sequence modification(s) outside the CDR regions as defined above in one or both of the heavy chain and light chain variable domains, in addition to the up to 12 amino acid sequence modification(s) at any of positions 1-30, 36-49, 67-97 and 104-115 of SEQ ID NO: 29 or the up to 10 amino acid sequence modification(s) between positions 1-23, 35-49, 57-88 and 98-107 of SEQ ID NO: 31. That is to say, the present invention encompasses a heavy chain variable domain comprising the sequence given in SEQ ID NO:29 having up to 15 amino acid sequence modification(s) outside the CDR regions as defined above and/or a light chain variable domain comprising the sequence given in SEQ ID NO:31 having up to 13 amino acid sequence modification(s) outside the CDR regions as defined above.

For example, 0, 1 or 2 residues outside the CDR regions in the heavy chain comprising the sequence given in SEQ ID NO:30, and 0, 1 or 2 residues outside the CDR regions in the light chain comprising the sequence given in SEQ ID NO:32, can be replaced by another amino acid. For example, 0 or 1 residues outside the CDR regions in the heavy chain can be replaced by another amino acid. For example, 0 or 1 residues outside the CDR regions in the light chain can be replaced by another amino acid. Preferably, no residues in the Sequences SEQ ID NO: 30 and 32 are varied to amino acids other than the ones specifically recited.

For example, SEQ ID NO: 29 or 30 can be the sequence of SEQ ID:5, SEQ ID:7, SEQ ID:9, or SEQ ID:11.

In SEQ ID NO:30, it is preferred that:
$X^9$ is A, $X^{11}$ is V, $X^{24}$ is A or T, $X^{38}$ is R or K, $X^{41}$ is P, $X^{55}$ is N or Q, $X^{68}$ is V or A, $X^{70}$ is I, and $X^{86}$ is L or P. For example, SEQ ID NO:30 can be the sequence of SEQ ID:5, SEQ ID:7, SEQ ID:9, or SEQ ID:11.

In SEQ ID NO:30, it is further preferred that:
$X^9$ is A, $X^{11}$ is V, $X^{24}$ is A, $X^{38}$ is R, $X^{41}$ is P, $X^{55}$ is N or Q, $X^{68}$ is V, $X^{70}$ is I and $X^{86}$ is L or P. For example, SEQ ID NO:30 can be the sequence of SEQ ID:5, SEQ ID:7, SEQ ID:9, or SEQ ID:11.

In particular, it is especially preferred that:
$X^9$ is A, $X^{11}$ is V, $X^{24}$ is A, $X^{38}$ is R, $X^{41}$ is P, $X^{55}$ is N, $X^{68}$ is V, $X^{70}$ is I and $X^{86}$ is L. For example, SEQ ID NO:30 can be the sequence of SEQ ID:5, SEQ ID:7, or SEQ ID:9.

An alternative especially preferred embodiment is when:
$X^9$ is A, $X^{11}$ is V, $X^{24}$ is A, $X^{38}$ is R, $X^{41}$ is P, $X^{55}$ is N, $X^{68}$ is V, $X^{70}$ is I and $X^{86}$ is P. For example, SEQ ID NO:30 can be the sequence of SEQ ID:11.

In SEQ ID NO:32, it is preferred that:
$X^3$ is Q or V, $X^{10}$ is T $X^{63}$ is S or T, $X^{80}$ is P or S, $X^{85}$ is V or D, $X^{87}$ is Y or F and $X^{103}$ is K. For example, SEQ ID NO:32 can be the sequence of SEQ ID:6, SEQ ID:8 or SEQ ID:10.

In SEQ ID NO:32, it is further preferred that:
$X^3$ is Q or V, $X^{10}$ is T, $X^{63}$ is S, $X^{80}$ is P, $X^{85}$ is V or D, $X^{87}$ is Y and $X^{103}$ is K. For example, SEQ ID NO:32 can be the sequence of SEQ ID:6, SEQ ID:8 or SEQ ID:10.

In SEQ ID NO:32, it is especially preferred that:
$X^3$ is Q, $X^{10}$ is T, $X^{63}$ is S, $X^{80}$ is P, $X^{85}$ is V, $X^{87}$ is Y and $X^{103}$ is K. For example, SEQ ID NO:32 can be the sequence of SEQ ID:6, SEQ ID:8 or SEQ ID:10.

In a preferred embodiment, the antibody of the present invention comprises a variable domain heavy chain having the sequence of SEQ ID:5, SEQ ID:7, SEQ ID:9, or SEQ ID:11 and a variable domain light chain having the sequence of SEQ ID:6, SEQ ID:8 or SEQ ID:10.

For example, the antibody of the present invention comprises a variable domain heavy chain of SEQ ID NO:5 and a variable domain light chain of SEQ ID NO:6 (referred to as 'AB-02'); or a variable domain heavy chain of SEQ ID NO:7 and a variable domain light chain of SEQ ID NO:8 (referred to as 'AB-03'); or a variable domain heavy chain of SEQ ID NO:9 and a variable domain light chain of SEQ ID NO:8 (referred to as 'AB-04'); or a variable domain heavy chain of SEQ ID NO:5 and a variable domain light chain of SEQ ID NO:10 (referred to as 'AB-05'); or a variable domain heavy chain of SEQ ID NO:11 and a variable domain light chain of SEQ ID NO:10 (referred to as 'AB-06'); or a variable domain heavy chain of SEQ ID NO:12 and a variable domain light chain of SEQ ID NO:10 (referred to as 'AB-07').

The present invention also provides an antibody or antigen-binding portion thereof which binds to PSMA and comprises a heavy chain variable domain comprising a CDR3 having the sequence $X^{2-5}DY$ (SEQ ID NO: 35) wherein $X^{2-5}$ is YWLF (SEQ ID NO: 39), GWTF (SEQ ID NO: 40) or AWTM (SEQ ID NO: 41),
and wherein
if $X^{2-5}$ is GWTF (SEQ ID NO: 40) or AWTM (SEQ ID NO: 41), the amino acid residue at position H94 in the heavy chain variable region, based on Kabat numbering, is G; and if $X^{2-5}$ is YWLF (SEQ ID NO: 39), the amino acid residue at position H94 in the heavy chain variable region, based on Kabat numbering, is A,
and optionally one or both of the sequences

CDR1: EYTIH (SEQ ID NO: 33)

CDR2: NINPNX¹GGTTYNQKFED, (SEQ ID NO: 34)

wherein $X^1$ is N or Q.
Preferably, $X^1$ is N

The present invention also provides an antibody or antigen-binding portion thereof which binds to PSMA and comprises a light chain variable domain comprising a CDR3 having the sequence $QQX^{1-5}LT$ (SEQ ID NO: 38) wherein $X^{1-5}$ is FTRYP (SEQ ID NO: 45) or YNAYS (SEQ ID NO: 46).
and optionally one or both of the sequences

CDR1: KASQDVGTAVD (SEQ ID NO: 36)

CDR2: WASTRHT. (SEQ ID NO: 37)

The present invention also provides an antibody or antigen-binding portion thereof which binds to PSMA and comprises:
a heavy chain variable domain comprising the sequences:

CDR1: EYTIH (SEQ ID NO: 33)

CDR2: NINPNX¹GGTTYNQKFED (SEQ ID NO: 34)

CDR3: $X^{2-5}DY$ (SEQ ID NO: 35)

wherein
$X^1$ is N or Q, preferably N, and
$X^{2-5}$ is YWLF (SEQ ID NO: 39), GWTF (SEQ ID NO: 40) or AWTM (SEQ ID NO: 41),
and wherein
if $X^{2-5}$ is GWTF (SEQ ID NO: 40) or AWTM (SEQ ID NO: 41), the amino acid residue at position H94 in the heavy chain variable region, based on Kabat numbering, is G; and
if $X^{2-5}$ is YWLF (SEQ ID NO: 39), the amino acid residue at position H94 in the heavy chain variable region, based on Kabat numbering, is A,
and
a light chain variable domain comprising the sequences:

CDR1: KASQDVGTAVD (SEQ ID NO: 36)

CDR2: WASTRHT (SEQ ID NO: 37)

CDR3: $QQX^{1-5}LT$ (SEQ ID NO: 38)

wherein $X^{1-5}$ is FTRYP (SEQ ID NO: 45) or YNAYS (SEQ ID NO: 46).

The antibodies of the invention are humanised antibodies that bind to PSMA (for example human PSMA) with an equilibrium dissociation constant (Kd) of $10^{-8}$M or lower, for example $10^{-9}$M or lower, for example $750 \times 10^{-12}$M or lower, for example $500 \times 10^{-12}$M or lower. For example, antibodies of the invention specifically bind to a human prostate cancer cell.

The antibodies of the invention have improved stability compared with certain prior humanised (or de-immunised) anti-PSMA antibodies. The antibodies of the invention thus have less propensity to denature or aggregate, or disassociate into component fragments. It is hypothesised that, as a result, they remain in the circulation in a native conformation for longer. A reduced tendency to aggregate is a particular advantage for an antibody-drug conjugate, and for reagents that produce these conjugates; cytotoxic drugs tend to be hydrophobic and thus conjugation reagents and antibody-drug conjugates with cytotoxic drugs have a propensity to aggregate in solution, which significantly reduces their effectiveness. A fragmented antibody (including as part of an antibody-drug conjugate) loses its ability to bind to the target antigen. An antibody with a reduced susceptibility to fragmentation is thus also advantageous.

An antibody of the invention may have a heavy chain of isotype IgG1, IgG2, IgG3 or IgG4, IgM, IgA1, IgA2, IgAsec, IgD or IgE. IgG1, IgG2, IgG3 and IgG4 are especially preferred. Alternatively, it may have an altered IgG constant region, for example to increase or decrease binding to Fc receptors or to increase or decrease binding to complement, for example, the IgG constant region may be IgG4k or IgG1k. An antibody of the invention may have an antibody light chain that is a kappa light chain.

A compound of the invention may be full-length antibody (e.g., an IgG4 or IgG1 antibody). Alternatively, it can include only an antigen-binding portion. For example, a compound of the invention may be a Fab, F(ab'), F(ab')₂, a Fd chain, Fv fragment or a single chain Fv (scFv), a disulfide-linked Fv (sdFv), a fragment comprising only a VH domain, including nanobodies or fragments from camels, llamas or the like. The invention also provides bispecific and multispecific antibodies (two or more different antibody molecules joined together to give two or more different specificities) including at least one antibody or antigen-binding portion thereof as described hereinabove. The antigen-binding portion may for example be a minibody composed of different permutations of scFv fragments or diabodies and Fc fragments or $C_H$ domains such as scFv-Fc, scFv-Fc-scFv, (Fab' ScFv)$_2$, scDiabody-Fc, scDiabody-$C_H$3, scFv-$C_H$3, scFv-$C_H$2-$C_H$3 fusion proteins and so forth. An antibody fragment can be produced by enzymatic cleavage, synthetic or recombinant techniques.

An antibody or antigen-binding portion thereof of the invention may be produced by a mammalian cell line, especially CHO or NS0 cells. For example, an antibody of the invention may be a monoclonal antibody.

The antibodies or antigen-binding portions thereof of the invention find use as diagnostic or therapeutic agents in vivo and in vitro.

In another aspect, the invention provides nucleic acid molecules encoding the humanised antibodies or antigen-binding portions thereof, of the invention. Accordingly, recombinant expression vectors that include the antibody-encoding nucleic acids of the invention, and host cells transfected with such vectors, are also encompassed by the invention, as are methods of making the antibodies of the invention by culturing these host cells. For example, the antibodies or antigen-binding portions thereof of the invention can be encoded by human IgG heavy chain and human kappa light chain nucleic acids with sequences as set forth in SEQ ID NO: 21, 23, 25 or 27 (heavy chain) or SEQ ID NO: 22, 24 or 26 (light chain), or variants thereof.

For example, a variant nucleic acid may be determined to be within the scope of the invention where this includes sequences containing or substantially identical to SEQ ID NO: 21, 23, 25 or 27 for example as determined by its ability to hybridise under stringent conditions to a nucleic acid of the present invention, for example a nucleic acid of SEQ ID NO: 21, 23, 25 or 27. The term "hybridise" refers to the binding, duplexing, or hybridising of a molecule to a particular nucleotide sequence under stringent hybridisation conditions when that sequence is present in a complex mixture (e.g. total cellular or library DNA or RNA), wherein the particular nucleotide sequence is detected at least at about 10 times background. Stringent hybridisation conditions will be selected, for example, to be 5-10° C. lower than the thermal melting point (Tm) for the specific sequence at a defined ionic strength and pH. For example, stringent hybridisation conditions can be:

50% deionized formamide
2× Saline Sodium Citrate (SSC)*
50 mM Na2HPO4/NaH$_2$PO$_4$ buffer; pH 7.0
1 mM EDTA
target DNA/RNA (1 mg/ml each)
probe (approx. 20-200 ng/ml)
Temperature: 37 to 42° C.; Hybridization time: 5 minutes-16 hours
*SSC: 1×SSC=150 mM NaCl, 15 mM sodium citrate; pH 7.0.

Conjugates

The invention further provides an antibody or antigen-binding portion thereof, for example Fab, according to the invention, conjugated via a linker to a payload which may be another functional molecule, for example a therapeutic, diagnostic or labelling agent, and/or a polymer. A single molecule of another functional molecule may be present, or two or more molecules may be present. It is often preferred that antibody drug conjugates should contain multiple copies of the drug. The functional molecule may for example be another peptide or protein, e.g. a Fab' fragment. The inclusion of one or more drug molecules, for example a cytotoxic agent or a toxin, is preferred. Auristatins and maytansinoids are typical cytotoxic drugs. Labelling agents (which should be understood to include imaging agents) may for example include a radionuclide, a fluorescent agent (for example an amine derivatised fluorescent probe such as 5-dimethylami-nonaphthalene-1-(N-(2-aminoethyl))sulfonamide-dansyl ethylenediamine, Oregon Green® 488 cadaverine (catalogue number 0-10465, Molecular Probes), dansyl cadaverine, N-(2-aminoethyl)-4-amino-3,6-disulfo-1,8-naphthalim-ide, dipotassium salt (lucifer yellow ethylenediamine), or rhodamine B ethylenediamine (catalogue number L 2424, Molecular Probes), or a thiol derivatised fluorescent probe for example BODIPY® FL L-cystine (catalogue number B-20340, Molecular Probes). The labelling agent may also be a dye, a contrast agent, a bioluminescent agent, an enzyme, an enhancing agent, or a nanoparticle. Biotin may also be used.

In some embodiments, an antibody or antigen-binding portion thereof is conjugated to a therapeutic agent. A "therapeutic agent" as used herein is an atom, molecule, or compound that is useful in the treatment of a disease or condition mediated by PSMA or characterised by increased expression of PSMA. Examples of therapeutic agents include, but are not limited to, drugs, chemotherapeutic agents, therapeutic antibodies and antibody fragments, toxins, radioisotopes, enzymes (for example, enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles.

In some embodiments, a therapeutic approach includes radioimmunotherapy by attaching an appropriate radiolabel such as, Iodine-131, a beta-emitter, such as, Yttrium-90, Lutetium-177, Copper-67, Astatine-211, Lead-212/Bismuth-212, Actinium-225/Bismuth-213, and Thorium, which can deliver cell damage and death to a target tissue.

In some embodiments, nanoparticles are used in therapeutic applications as drug carriers that, when conjugated to an antibody or antigen-binding portion thereof, deliver chemotherapeutic agents, hormonal therapeutic agents, radiotherapeutic agents, toxins, or any other cytotoxic or anticancer agent known in the art to cancerous cells that overexpress PSMA. Any of the antibodies or antigen-binding portions thereof described herein may be further conjugated with one or more additional therapeutic agents, detectable markers, nanoparticles, carriers or a combination thereof. For example, an antibody or antigen-binding portion thereof may be radiolabeled with Iodine-131 and conjugated to a lipid carrier, such that the anti-PSMA-lipid conjugate forms a micelle. The micelle can incorporate one or more therapeutic or detectable markers. Alternatively, in addition to the carrier, the antigen binding construct may be radiolabeled with Iodine-131 I (for example, at a tyrosine residue) and conjugated to a drug (for example, at the epsilon amino group of a lysine residue), and the carrier may incorporate an additional therapeutic or detectable marker.

In some embodiments, antigen-binding portions of the invention are conjugated to a therapeutic agent. While these antigen-binding portions can have a shorter circulation half-life compared to a full-length antibody, in some embodiments, these formats can exhibit improved tumor penetration based on their smaller size and be therapeutically effective when appropriately armed with a cytotoxic drug or radioisotope. In some embodiments, an antibody drug-conjugate approach can be employed. In some embodiments, treatment with these fragments armed with a cytotoxic drug or radionuclide result in less nonspecific toxicity as they will be cleared from the body more rapidly.

In some embodiments, an antibody or antigen-binding portion thereof is conjugated to a detectable marker. As used herein, a "detectable marker" includes an atom, molecule, or compound that is useful in diagnosing, detecting or visualizing a location and/or quantity of a PSMA antigen in a cell, tissue, organ or the like. Detectable markers that can be used in accordance with the embodiments herein include, but are not limited to, radioactive substances (for example, radioisotopes, radionuclides, radiolabels or radiotracers), dyes, contrast agents, fluorescent compounds or molecules, bioluminescent compounds or molecules, enzymes and enhancing agents (for example, paramagnetic ions). In addition, some nanoparticles, for example quantum dots and metal nanoparticles are known in the art to be suitable for use as a detection agent. In some embodiments, the detectable marker is IndoCyanine Green (ICG), Zirconium-89, IR800, and/or another near infrared dye.

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{94}$Tc, $^{99m}$TC, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Ab, $^{211}$At, $^{211}$Pb, $^{212}$Bi, $^{212}$Pb, $^{231}$Bi, $^{223}$Ra and $^{225}$Ac. Exemplary paramagnetic ions substances that can be used as detectable markers include, but are not limited to ions of transition and lanthanide metals (for example metals having atomic numbers of 6-9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Exemplary contrast agents that can be used as detectable markers in accordance with the embodiments of the disclosure include, but are not limited to, barium, diatrizoate, ethiodised oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable markers in accordance with the embodiments of the disclosure include, but are not limited to, fluorescein, fluorescein isothiocyanate (FITC), OREGON GREEN™, rhodamine, Texas red, tetrarhodimine isothiocynate (TRITC), Cy3, Cy5, and the like, fluorescent markers (for example, green fluorescent protein (GFP), phycoerythrin, and the like), autoquenched fluorescent compounds that are activated by tumour-associated proteases, enzymes (for example, luciferase, horseradish peroxidase, alkaline phosphatase, and the like), nanoparticles, biotin, digoxigenin or combination thereof.

Enzymes that can be used as detectable markers in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

Suitable linkers for attaching the payload to the antibody or antigen-binding portion thereof are those described in the section on Conjugating Reagents below. The linker is advantageously degradable, as described below. In some preferred embodiments, the linker includes a polymer, as described below.

Preferred conjugates according to the invention are those in which the bonding of the payload to the antibody or antigen-binding portion thereof is via a bonding portion which has the general formula:

(I)

in which Pr represents said antibody or antigen-binding portion thereof, each Nu represents a nucleophile present in or attached to the antibody or antigen-binding portion thereof, each of A and B independently represents a $C_{1-4}$alkylene or alkenylene chain, and W' represents an electron withdrawing group or a group obtained by reduction of an electron withdrawing group.

An electron withdrawing group W' may for example be a keto group —CO—, an ester group —O—CO— or a sulfone group —SO$_2$—. Preferably W' represents one of these groups or a group obtainable by reduction of one of these groups as described below. Preferably W' represents a keto group or a group obtainable by reduction of a keto group, especially a CH.OH group.

Preferably the grouping has the formula:

(Ia)

especially

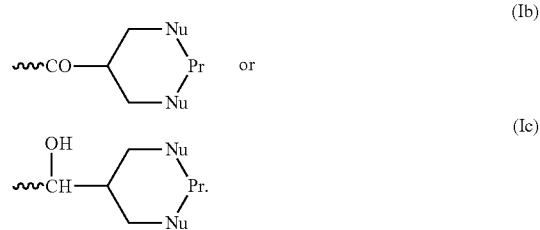

(Ib)

(Ic)

Nucleophilic groups in the antibody or antigen-binding portion thereof are for example provided by cysteine, lysine or histidine residues, and Nu may for example be a sulfur atom or an amine group. In one preferred embodiment of the invention, each Nu represents a sulfur atom present in a cysteine residue present in the antibody or antigen-binding portion thereof. The antibody according to the invention will generally contain four interchain disulphide bonds. Each of these may be reduced to provide free thiol groups which act as nucleophiles. If each of these disulphide bonds is bridged as shown in the formulae I above, a conjugate with a drug-antibody ratio (DAR) of 4 will be produced. In another embodiment, each Nu represents an imidazole group present in a histidine residue present in a polyhistidine tag attached to said antibody or antigen-binding portion thereof.

The conjugate of the invention may, for example, be of the general formula:

(III)

in which D represents the payload;
q represents an integer from 1 to 10;
$Lk^1$ represents a linker;
r represents an integer from 1 to 10;
$P^1$ represents a bond or a c-valent group —$P^2$—NH— where c is from 2 to 11 and $P^2$ is a group containing at least one ethylene unit —$CH_2$—$CH_2$— or ethylene glycol unit —O—$CH_2$—$CH_2$—;
e represents an integer from 1 to 10;
$Lk^2$ represents a bond or a d-valent linker where d is from 2 to 11 and which consists of from 1 to 9 aspartate and/or glutamate residues;
$Lk^3$ represents a linker of the general formula:

—CO-Ph-Y—Z— (AII)

in which Ph is an optionally substituted phenyl group; Y represents a CO group or a CH.OH group; and Z represents a group of formula:

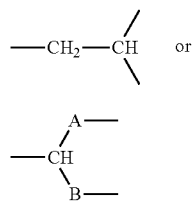

(AIII)

or (AIV)

in which each of A and B represents a $C_{1-4}$alkylene or alkenylene group; Ab represents the antibody or antigen-binding portion thereof according to the invention, being bonded to $Lk^3$ via two sulfur atoms derived from a disulfide bond in the antibody or antigen-binding portion thereof; and e represents an integer from 1 to s where s is the number of disulfide bonds present in the antibody or antigen-binding portion thereof prior to conjugating to $Lk^3$.

The meanings of q, r, e, c and d determine the total number of D groups present. This number may for example be up to 20, for example up to 15, for example up to 10, for example 1, 2, 3 or 4.

Conjugating Reagents

Conjugates according to the invention may be prepared by reacting a conjugating reagent with an antibody or an antigen-binding portion thereof according to the invention. The conjugation may for example be carried out by chemical coupling, genetic fusion, non-covalent association or otherwise, but is preferably carried out by chemical coupling.

Typically, the conjugating reagent will comprise a functional group capable of covalently reacting with at least one electrophile or, especially, nucleophile present in the antibody or an antigen-binding portion thereof, which functional group is attached to a payload via a linker. Many conjugating reagents which can be used to conjugate a payload to an antibody or an antigen-binding portion thereof are known, and any of these may be used to prepare a conjugate according to the invention.

For example, the reagent may contain a maleimide group, a click-chemistry group, for example an azide or alkyne group, an amine group, a carboxyl group, or an active ester group. Other possible approaches include the use of antibodies that have been recombinantly engineered with an amino acid specifically for conjugation such as engineered cysteines or non-natural amino acids, and enzymatic conjugation through a specific enzymatic reaction such as with transglutaminase. The reaction site on the antibody or an antigen-binding portion thereof may be either nucleophilic or electrophilic in nature. Common protein conjugation sites are at lysine or cysteine amino acid residues or carbohydrate moieties. Alternatively, conjugation may occur at a polyhistidine tag which has been attached to the antibody or an antigen-binding portion thereof.

A conjugating reagent is advantageously capable of reacting with a nucleophile in the antibody or an antigen-binding portion thereof and hence becoming chemically bonded thereto. As such the conjugating reagent typically includes at least one leaving group which is lost on reaction with a nucleophile. The conjugating reagent may, for example, include two or more leaving groups. Preferably the conjugating reagent is capable of reacting with two nucleophiles. Advantageously, the conjugating reagent comprises at least two leaving groups. If two or more leaving groups are present, these may be the same or different. Alternatively, a conjugating reagent may contain a single group which is chemically equivalent to two leaving groups and which single group is capable of reacting with two nucleophiles.

One group of reagents is based on the bis-halo- or bis-thio-maleimides and derivatives thereof as described in Smith et al., *J. Am. Chem. Soc.*, 2010, 132, 1960-1965, and Schumacher et al., *Bioconj. Chem.*, 2011, 22, 132-136. These reagents contain the functional grouping:

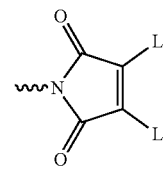

in which each L is a leaving group. The nitrogen atom of the maleimide ring may carry the payload, directly or indirectly.

Similarly, maleimides containing a single leaving group L:

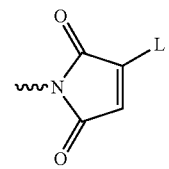

may be used. Again, the nitrogen atom of the maleimide ring carries the payload, directly or indirectly.

Also, maleimides lacking a leaving group:

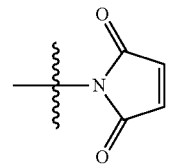 [SMILES: *N1C(=O)C=CC1=O]

may be used. Again, the nitrogen atom of the maleimide ring carries the payload, directly or indirectly.

In a preferred embodiment, a conjugating reagent contains the functional grouping:

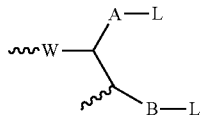

(CI)

in which W represents an electron-withdrawing group, for example a keto group, an ester group —O—CO—, a sulfone group —$SO_2$—, or a cyano group; A represents a $C_{1-5}$ alkylene or alkenylene chain; B represents a bond or a $C_{1-4}$ alkylene or alkenylene chain; and either each L independently represents a leaving group, or both Ls together represent a leaving group. Reagents of this type are described in *Bioconj. Chem* 1990(1), 36-50, *Bioconj. Chem* 1990(1), 51-59, and *J. Am. Chem. Soc.* 110, 5211-5212. When reagents containing such groups react with the antibody or an antigen-binding portion thereof, a first leaving group L is lost to form in situ a conjugating reagent containing a functional grouping of formula:

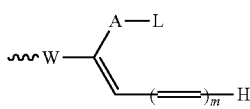

(CI')

in which m is 0 to 4, which reacts with a first nucleophile. The second leaving group L is then lost, and reaction with a second nucleophile occurs. As an alternative to using a reagent containing the functional grouping CI as starting material, reagents containing the functional grouping CI' may be used as starting material.

Preferably W represents a keto group. Preferably A represents —$CH_2$— and B represents a bond.

Particularly preferred functional groupings of formula CI and CI' have the formulae:

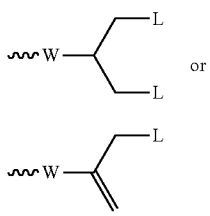

(CIa)

or (CIa')

For example, the group may be of the formula:

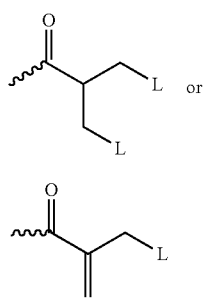

(CIb)

or (CIb')

Another group of conjugating reagents contains the functional grouping:

~W—$CR^4R^{4'}$—$CR^4$.L.L'    (CII)

in which W has the meaning and the preferred meanings given above, and either
    each $R^4$ represents a hydrogen atom or a $C_{1-4}$ alkyl group, $R^{4'}$ represents a hydrogen atom, and either each L independently represents a leaving group, or both Ls together represent a leaving group; or
    each $R^4$ represents a hydrogen atom or a $C_{1-4}$ alkyl group, $L^{4'}$ represents a leaving group, and $R^{4'}$ and L' together represent a bond.

Another group of conjugating reagents includes the functional grouping:

~W—(CH=CH)$_p$—(CH$_2$)$_2$-L    (CIII) or

~W—(CH=CH)$_p$—CH=CH$_2$    (CIII')

in which W has the meaning and preferred meanings given above and p represents 0 or an integer of from 1 to 4, preferably 0. An especially preferred reagent of this type includes the functional grouping:

~NH—CO—Ar—CO—(CH$_2$)$_2$-L    (CIIIa) or

~NH—CO—Ar—CO—CH=CH$_2$    (CIIIa')

in which Ar represents an optionally substituted aryl, especially phenyl, group.

A leaving group L may for example be —SP, —OP, —$SO_2$P, —$OSO_2$P, —$N^+PR^2R^3$, halogen, —OØ, in which P represents a hydrogen atom, an alkyl (preferably $C_{1-6}$alkyl), aryl (preferably phenyl), or alkyl-aryl (preferably $C_{1-6}$alkyl-phenyl) group, or is a group which includes a portion —(CH$_2$CH$_2$O)$_n$— in which n is a number of two or more, especially 6 or more, and each of $R^2$ and $R^3$ independently represents a hydrogen atom, a $C_{1-4}$alkyl group, or a group P, and Ø represents a substituted aryl, especially phenyl, group, containing at least one substituent, for example —CN, —$CF_3$, —$NO_2$, —$CO_2R'$, —COH, —$CH_2OH$, —COR', —OR', —OCOR', —$OCO_2R'$, —SR', —SOR', —$SO_2R'$, —NHCOR', —NR'COR, —$NHCO_2R'$, —$NR'CO_2R$, —NO, —NHOH, —NR'OH, —CH=N—NR'COR', —$N^+R'_3$, halogen, especially chlorine or, especially, fluorine, —C≡CR and —CH=CR'$_2$, in which each R represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is preferred.

Conjugating reagents in which P represents a group which includes a portion —(CH$_2$CH$_2$O)$_n$—in which n is a number of two or more are the subject of our copending application GB 1418186.1, from which PCT/GB2015/052952, now published as WO2016/059377, claims priority. This application discloses the following:

"The leaving group may for example include —(CH$_2$CH$_2$O)$_n$—$R^1$ where $R^1$ is a capping group. A very wide range of capping groups may be used. $R^1$ may for example be a hydrogen atom, an alkyl group, especially a $C_{1-4}$alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —CH$_2$CH$_2$CO$_2$H or —CH$_2$CH$_2$NH$_2$, and may be prepared by functionalising the terminal unit of a —(CH$_2$CH$_2$O)$_n$— chain.

Alternatively, rather than being terminated by a capping group, the —(CH$_2$CH$_2$O)$_n$— group may have two points of attachment within the conjugating reagent such that chemically the equivalent of two leaving groups are present, capable of binding to two nucleophiles.

The —(CH$_2$CH$_2$O)$_n$— portion of the leaving group is based on PEG, polyethylene glycol. The PEG may be straight-chain or branched, and it may be derivatised or functionalised in any way. n is a number of 2 or more, for example 2, 3, 4, 5, 6, 7, 8, 9 or 10. For example, n may be from 5 to 9. Alternatively, n may be a number of 10 or more. There is no particular upper limit for n. n may for example be 150 or less, for example 120 or less, for example 100 or less. For example n may be from 2 to 150, for example from 7 to 150, for example from 7 to 120. The PEG portion —(CH$_2$CH$_2$O)$_n$— of a leaving group may for example have a molecular weight of from 1 to 5 kDa; it may for example be 1 kDa, 2 kDa, 3 kDa, 4 kDa or 5 kDa. A leaving group may if desired contain two or more portions —(CH$_2$CH$_2$O)$_n$— separated by one or more spacers.

A leaving group in a reagent according to the invention is suitably of the formula —SP, —OP, —SO$_2$P, —OSO$_2$P, —N$^+$PR$^2$R$^3$, in which P is a group which includes a portion —(CH$_2$CH$_2$O)$_n$— and each of R$^2$ and R$^3$ independently represents a hydrogen atom, a C$_{1-4}$alkyl group, or a group P. Preferably each of R$^2$ and R$^3$ represents a C$_{1-4}$alkyl group, especially a methyl group, or, especially, a hydrogen atom. Alternatively, the conjugating reagent may include a group of formula —S—P—S—; —O—P—O—; —SO$_2$—P—SO$_2$—; —OSO$_2$—P—OSO$_2$—; and —N$^+$R$^2$R$^3$—P—N$^+$R$^2$R$^3$—. Specific groups of this type include —S—(CH$_2$CH$_2$O)$_n$—S—, —O—(CH$_2$CH$_2$O)$_n$—O—; —SO$_2$—(CH$_2$CH$_2$O)$_n$—SO$_2$—; —OSO$_2$—(CH$_2$CH$_2$O)$_n$—OSO$_2$—; or —N$^+$R$^2$R$^3$—(CH$_2$CH$_2$O)$_n$—N$^+$R$^2$R$^3$—. They can also include groups of the type:

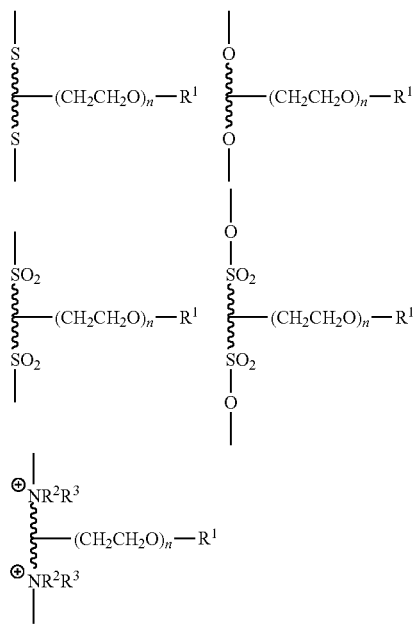

where the —(CH$_2$CH$_2$O)$_n$— group is carried by any suitable linking group, for example an alkyl group.

These divalent groups are chemically equivalent to two leaving groups capable of reacting with two nucleophiles."

An especially preferred leaving group L present in a conjugating reagent is —SP or —SO$_2$P, especially —SO$_2$P. Within this group, one preferred embodiment is where P represents a phenyl or, especially, a tosyl group. Another preferred embodiment is where P represents a group which includes a portion —(CH$_2$CH$_2$O)$_n$—, especially one in which n has one of the values mentioned above, especially 7. An especially preferred leaving group L is —SO$_2$—(CH$_2$CH$_2$O)$_n$—H/Me, especially —SO$_2$—(CH$_2$CH$_2$O)$_7$—H/Me. Throughout this Specification, any reference to a leaving group L should be understood to include a specific reference to these preferred groups, especially —SO$_2$—(CH$_2$CH$_2$O)$_n$—H/Me, and more especially —SO$_2$—(CH$_2$CH$_2$O)$_7$—H/Me.

Conjugating reagents may contain more than one functional group. For example, a reagent may contain a functional grouping of type C above at one end of the molecule, and one or more additional functional groupings, either capable of conjugating with the antibody or an antigen-binding portion thereof or any other molecule, elsewhere in the molecule. Such structures are described in for example Belcheva et al, *J. Biomater. Sci Polymer Edn.* 9(3), 207-226 and are useful in the synthesis of conjugates containing multiple proteins.

Conjugating reagents containing the unit of formula CI/CI' may have the formula (CIc) or (CIc') or, where W represents a cyano group, (CId) or (CId'):

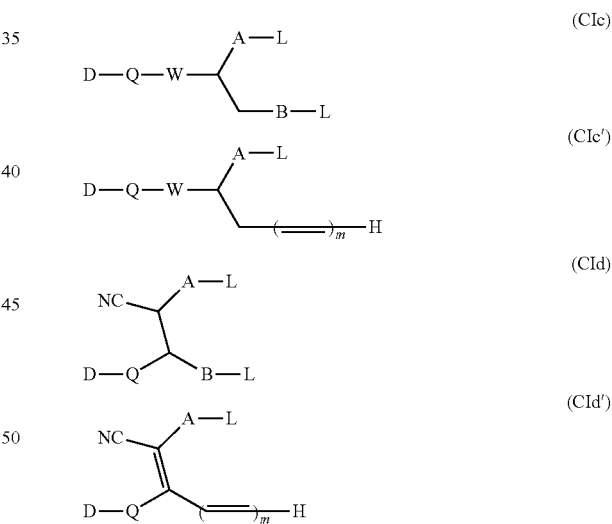

in which D represents a payload and Q represents a linking group.

Preferred conjugating reagents include the following:

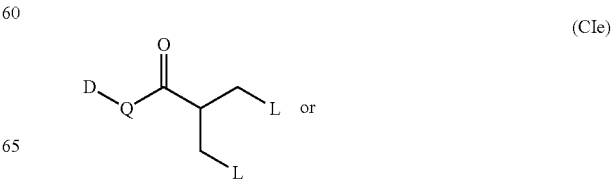

-continued

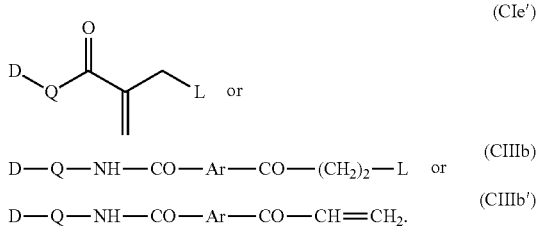
(CIe')

D—Q—NH—CO—Ar—CO—(CH$_2$)$_2$—L   or  (CIIIb)

D—Q—NH—CO—Ar—CO—CH=CH$_2$.  (CIIIb')

in which D represents the payload and Q represents a linking group.

The conjugating reagent may, for example, be of the general formula:

(II)

in which D represents the payload;
q represents an integer from 1 to 10; Lk' represents a linker;
r represents an integer from 1 to 10;
P$^1$ represents a bond or a c-valent group —P$^2$—NH— where c is from 2 to 11 and P$^2$ is a group containing at least one ethylene unit —CH$_2$—CH$_2$— or ethylene glycol unit —O—CH$_2$—CH$_2$—;
z represents an integer from 1 to 10;
Lk$^2$ represents a bond or a d-valent linker where d is from 2 to 11 and which consists of from 1 to 9 aspartate and/or glutamate residues;
Lk$^3$ represents a linker of the general formula:

—CO-Ph-Y—Z— (EII)

in which Ph is an optionally substituted phenyl group; Y represents a CO group or a CH(OH) group; and Z represents a group of formula:

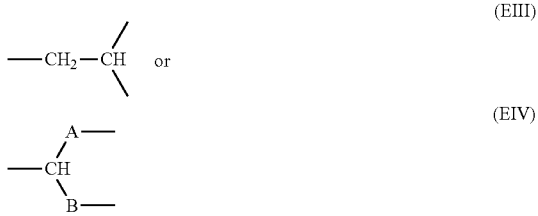
(EIII)

(EIV)

in which each of A and B represents a C$_{1-4}$alkylene or alkenylene group; and
in which L is a leaving group, for example one of those described below.

Any suitable linking group Q or Lk$^1$ may be used. In one embodiment, Q or Lk$^1$ may for example be a direct bond, an alkylene group (preferably a C$_{1-10}$ alkylene group), or an optionally-substituted aryl or heteroaryl group, any of which may be terminated or interrupted by one or more oxygen atoms, sulfur atoms, —NR" groups (in which R" represents a hydrogen atom or an alkyl (preferably C$_{1-6}$alkyl), aryl (preferably phenyl), or alkyl-aryl (preferably C$_{1-6}$alkyl-phenyl) group), keto groups, —OCO— groups, —COO— groups, —O—CO—O, —O—CO—NR"—, —NR"COO—, —CONR"— and/or —NR"CO— groups. Such aryl and heteroaryl groups Q form one preferred embodiment of the invention. Suitable aryl groups include phenyl and naphthyl groups, while suitable heteroaryl groups include pyridine, pyrrole, furan, pyran, imidazole, pyrazole, oxazole, pyridazine, pyrimidine and purine. Especially suitable linking groups Q or Lk$^1$ are heteroaryl or, especially, aryl groups, especially phenyl groups. These may have a linking group to the therapeutic agent D, for example a group which is, or contains, an —NR"—CO— or —CO—NR"— group, for example an —NH—CO— or —CO—NH— group.

Substituents which may be present on an optionally substituted aryl, especially phenyl, or heteroaryl group include for example one or more of the same or different substituents selected from alkyl (preferably C$_{1-4}$alkyl, especially methyl, optionally substituted by OH or CO$_2$H), —CN, —NO$_2$, —CF$_3$, NR"$_2$, —CO$_2$R", —COH, —CH$_2$OH, —COR", —OR", —OCOR", —OCO$_2$R", —SR", —SOR", —SO$_2$R", —NR"COR", —NR".CO$_2$R", —NO, —NHOH, —NR".OH, —CH=N—NR".CO R", —N$^+$R"$_3$, halogen, for example fluorine or chlorine, —C≡CR" and —CH=CR"$_2$, in which each R" independently represents a hydrogen atom or an alkyl (preferably C$_{1-6}$alkyl), aryl (preferably phenyl), or alkyl-aryl (preferably C$_{1-6}$alkyl-phenyl) group. The presence of electron withdrawing substituents is especially preferred. Preferred substituents include for example —CN, —CF$_3$, —NO$_2$, —OR", —OCOR", —SR", —NR"COR", —NHOH and —NR"CO$_2$R".

In another embodiment, a linker Lk, Q or Lk$^1$, or any other linker in a conjugate according to the invention, may contain a degradable group, i.e. it may contain a group which breaks under physiological conditions, separating the payload from the antibody or an antigen-binding portion thereof to which it is bonded. Alternatively, it may be a linker that is not cleavable under physiological conditions.

Suitable degradable linkers are discussed in more detail below.

The meanings of q, r, z, c and d determine the total number of D groups present. This number may for example be up to 20, for example up to 15, for example up to 10, for example 1, 2, 3 or 4.

Linkers

Conjugates of the invention and conjugating reagents suitable for preparing them contain a linker linking the antibody or antigen-binding portion thereof to the payload. This linker may be non-degradable or degradable under physiological conditions. Conjugates advantageously comprise a degradable linker which contains a group which breaks under physiological conditions, separating the payload from the antibody or antigen-binding portion thereof to which it is, or will ultimately be, bonded. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited). Suitable degradable linkers are discussed in more detail below.

Where a linker, for example Q or Lk', contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. Examples of groups susceptible to hydrolytic conditions include:

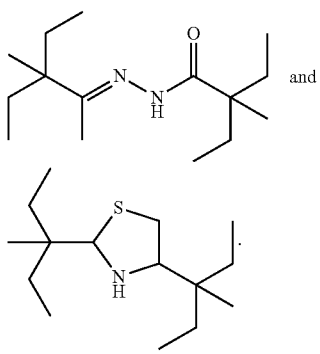
and

In a preferred embodiment, a linker, for example Q or Lk¹, is or includes

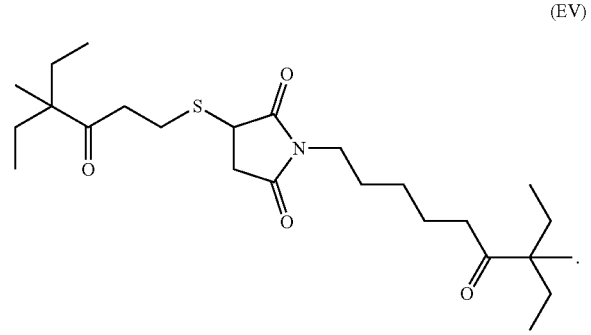 [SMILES: CCC(C)(CC)C(=O)CCCCCN1C(=O)CC(SCCC(=O)C(C)(CC)CC)C1=O]
(EV)

For example, a linker, for example Q or Lk¹ may be:

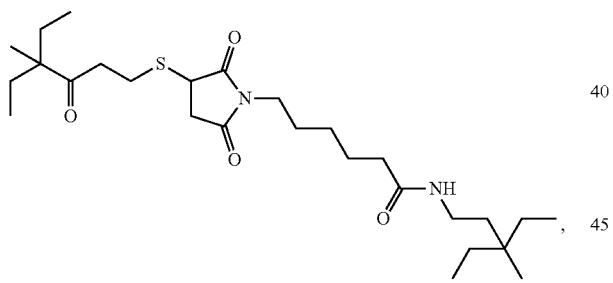
(EVa)

in which case it is preferably bonded to D and P¹ groups as shown:

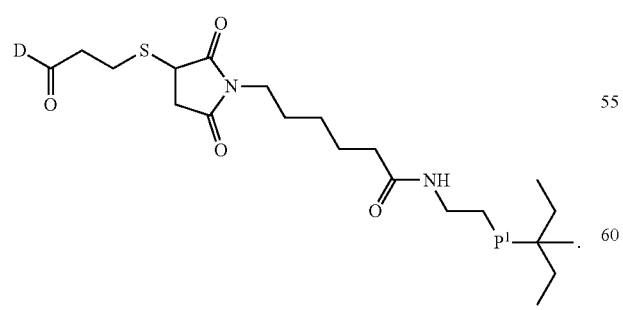

A linker may also be susceptible to degradation under reducing conditions. For example, it may contain a disulfide group that is cleavable on exposure to biological reducing agents, such as thiols. Examples of disulfide groups include:

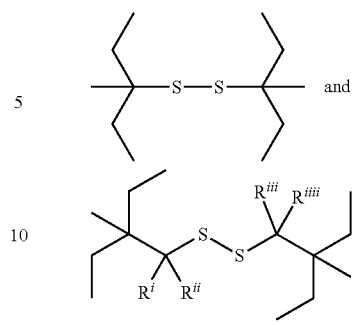
and in which $R^i$, $R^{ii}$ and $R^{iiii}$ are each independently hydrogen or $C_{1-4}$alkyl. In a preferred embodiment a linker, for example Q or Lk¹, is or includes

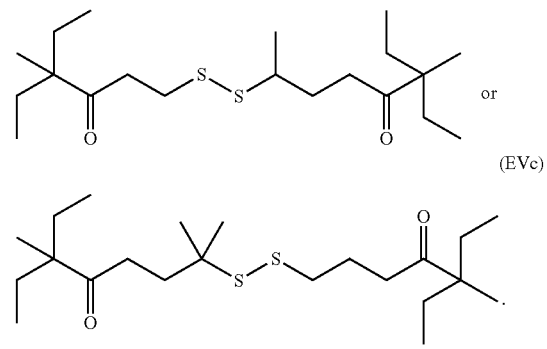
(EVb) or (EVc)

For example, it may be

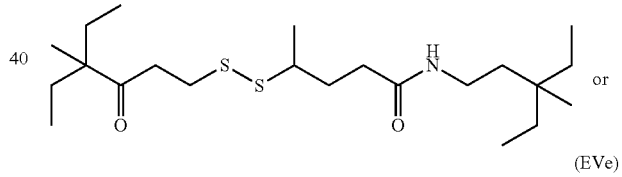
(EVd) or (EVe)

in which case the linker is preferably bonded to D and P¹ groups as shown:

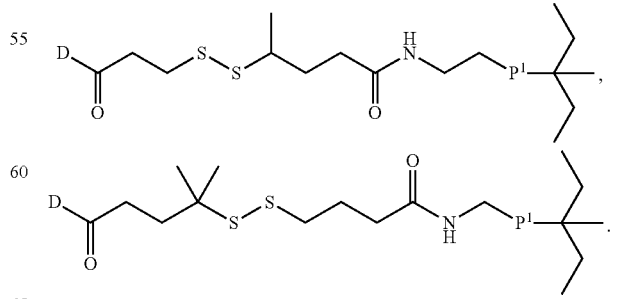

A linker, for example Q or Lk¹, may also contain a group which is susceptible to enzymatic degradation, for example it may be susceptible to cleavage by a protease (e.g. a lysosomal or endosomal protease) or peptidase. For example, it may contain a peptidyl group comprising at least one, for example at least two, or at least three amino acid residues (e.g. Phe-Leu, Gly-Phe-Leu-Gly, Val-Ala, Val-Cit, Phe-Lys). For example, it may be an amino acid chain having from 1 to 5, for example 2 to 4, amino acids.

Another example of a group susceptible to enzymatic degradation is:

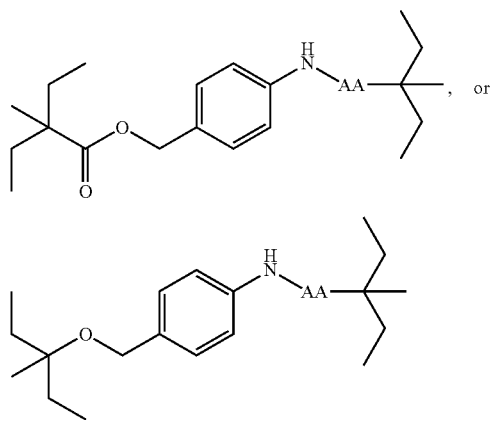

wherein AA represents an amino acid sequence, especially one containing 1 or two amino acid residues, especially a protease-specific amino acid sequence of two residues, such as Val-Cit.

In a preferred embodiment, the linker, for example Q or $Lk^1$, is or includes:

(EVf)

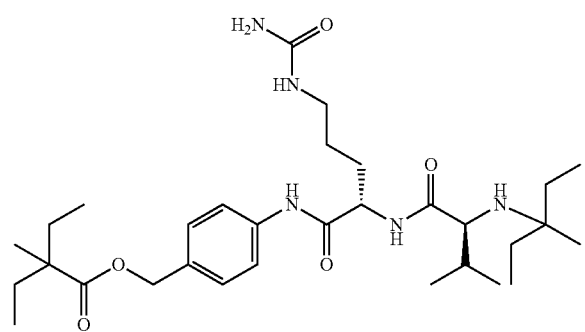

For example, it may be (EVg)

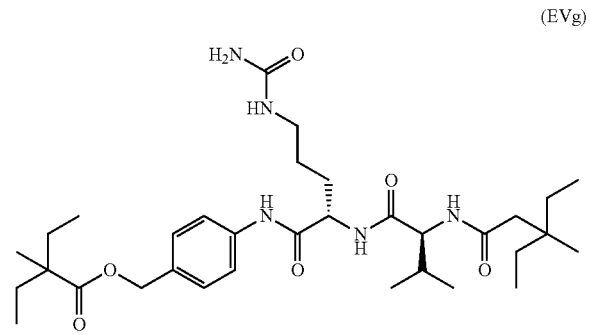 [SMILES: CCC(C)(CC)CC(=O)N[C@H](C(=O)N[C@@H](CCCNC(N)=O)C(=O)Nc1ccc(COC(=O)C(C)(CC)CC)cc1)C(C)C]

in which case it is preferably bonded to the payload D and $P^1$ groups as shown below

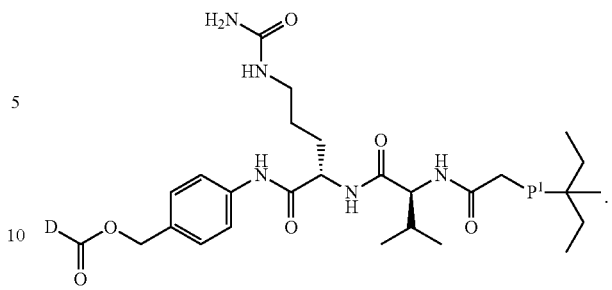

In one embodiment, a linker, for example Q or $Lk^1$, carries a single payload (i.e. q=1 in conjugating reagents of the formula (II)). The specific linkers (EVa), (EVd) and (EVe) shown above are of this type. In another embodiment, the linker carries multiple payloads (i.e. q>1, for example 2, 3 or 4, in conjugating reagents of the formula (II)) and the linker is used as a means of incorporating more than one copy of the therapeutic agent into a conjugate of the invention. In one embodiment, this may be achieved by the use of a branching linker $Lk^1$ and/or $Lk^2$, which may for example incorporate an aspartate or glutamate or similar residue. This introduces a branching element of formula:

(EVI)

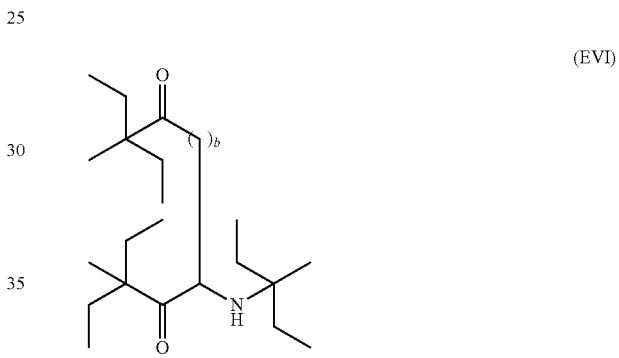

where b is 1, 2 or 3, b=1 being aspartate and b=2 being glutamate, and b=3 representing one preferred embodiment. Each of the acyl moieties in the formula EVI may be coupled to a payload via a suitable linker $Lk^{1a}$, where $Lk^{1a}$ is any suitable linker, for example a degradable linker incorporating one of the linkages mentioned above. In particular embodiments, $Lk^{1a}$ represents the group (EVa), (EVd) or (EVe) shown above. The amino group of the aspartate or glutamate or similar residue may be bonded to $P^1$ by any suitable means, for example the linkage may be via an amide bond, e.g. the branching group above may be connected to $P^1$ via a —CO—CH$_2$— group, thus:

(EVIa)

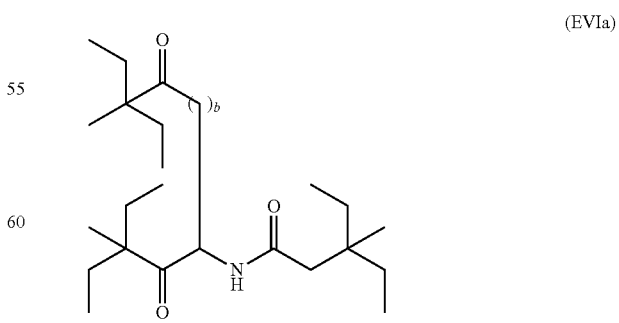

If desired, the aspartate or glutamate or similar residue may be coupled to further aspartate and/or glutamate and/or similar residues, for example:

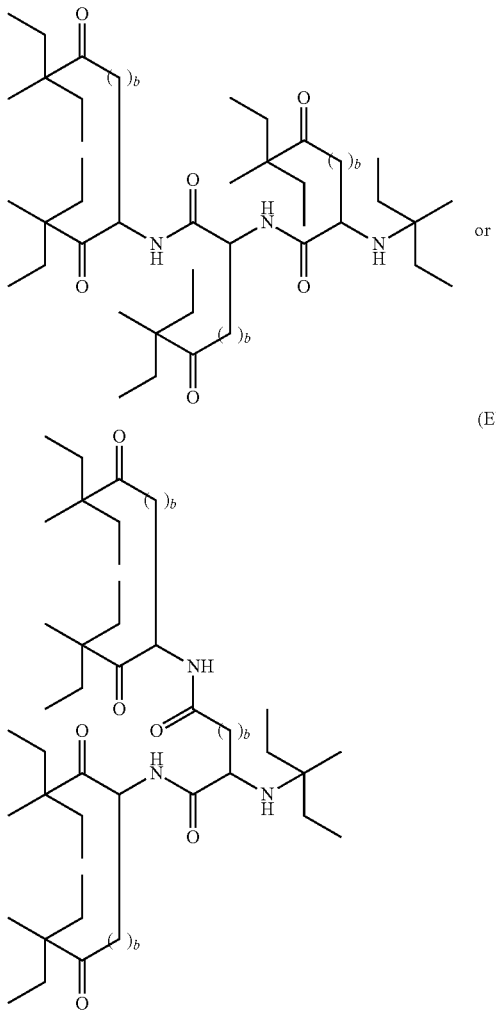

(EVIIa)

or (EVIIb)

and so on, giving the potential to incorporate many units of the therapeutic agent. As above, each payload unit may be attached to an aspartate/glutamate or similar residue via any suitable linker $Lk^{1a}$.

In a similar way, the amino acids lysine, serine, threonine, cysteine, arginine or tyrosine or similar residues may be introduced to form a branching group, thus:

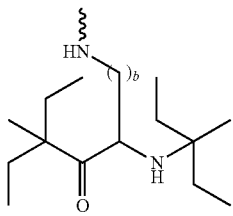

in which b is 4 for lysine, and

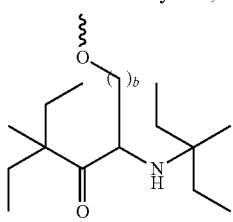

in which b is 1 for serine.

Polymers

The conjugates of the present invention may contain an oligomer or polymer (jointly referred to herein as "polymer" for convenience), together with the antibody or antigen-binding portion thereof according to the invention. For example, the antibody or antigen-binding portion thereof may be conjugated to a polymer via a linker. Alternatively, the linker may itself include a polymer, and this may be conjugated to the antibody or antigen-binding portion thereof. A polymer is especially a water soluble, synthetic polymer, particularly polyalkylene glycol. A polymer may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally, the polymer may be a polymer that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer may be a homopolymer, random copolymer or a structurally defined copolymer such as a block copolymer, for example it may be a block copolymer derived from two or more alkylene oxides, or from poly(alkylene oxide) and either a polyester, polyacetal, poly(ortho ester), or a poly(amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid), hyaluronic acid and derivatives thereof. Polymers such as polyglutamic acid may also be used, as may hybrid polymers derived from natural monomers such as saccharides or amino acids and synthetic monomers such as ethylene oxide or methacrylic acid.

If the polymer is a polyalkylene glycol, this is preferably one containing $C_2$ and/or $C_3$ units, and is especially a polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted, or capped, polyalkylene glycols, for example methoxypolyethylene glycol, may be used.

The polymer may, for example, be a comb polymer produced by the method described in WO 2004/113394, the contents of which are incorporated herein by reference. For example, the polymer may be a comb polymer having a general formula:

$(F)_f$-$(G)_g$-$(H)_h$ where:
F, where present, is obtainable by addition polymerisation of one or more olefinically unsaturated monomers which are not as defined in G;
G is obtainable by addition polymerisation of a plurality of monomers which are linear, branched, or star-shaped, substituted or non-substituted, and have an olefinically unsaturated moiety;
H, where present, is obtainable by addition polymerisation of one or more olefinically-unsaturated monomers which are not as defined in G;
f and h are an integer between 0 and 500;
g is an integer of 0 to 1000;
wherein at least one of F and G is present.

A polymer may optionally be derivatised or functionalised in any desired way. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. If desired, the polymer may be coupled to a solid support using conventional methods.

The optimum molecular weight of the polymer will of course depend upon the intended application. Long-chain polymers may be used, for example the number average molecular weight may be up to around 75,000, for example up to 50,000, 40,000 or 30,000 g/mole. For example, the number average molecular weight may be in the range of from 500 g/mole to around 75,000 g/mole. However, very small oligomers, consisting of discrete PEG chains with, for example, as few as 2 repeat units, for example from 2 to 50 repeat units, are useful for some applications, and are present in one preferred embodiment of the invention. For example, the polymer may contain from 2 to 48, for example from 2 to 36, for example from 2 to 24, units may be used. Straight chain or branched PEGs with 12, 20, 24, 36, 40 or 48 repeat units may for example be used. When the conjugate is intended to leave the circulation and penetrate tissue, for example for use in the treatment of inflammation caused by malignancy, infection or autoimmune disease, or by trauma, it may be advantageous to use a lower molecular weight polymer in the range up to 30,000 g/mole. For applications where the conjugate is intended to remain in circulation it may be advantageous to use a higher molecular weight polymer, for example in the range of 20,000-75,000 g/mole.

Preferably the polymer is a synthetic polymer, and preferably it is a water-soluble polymer. The use of a water-soluble polyethylene glycol is particularly preferred for many applications.

Our copending application GB 1418986.4 from which PCT/GB2015/052953 claims priority, published as WO2016/063006, relates to the use of PEG-containing linkers of a particular structure, and these may be used in the present invention. That application discloses the following:

"The invention provides a conjugate of a protein or peptide with a therapeutic, diagnostic or labelling agent, said conjugate containing a protein or peptide bonding portion and a polyethylene glycol portion; in which said protein or peptide bonding portion has the general formula:

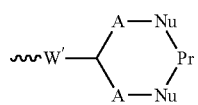

(I)

in which Pr represents said protein or peptide, each Nu represents a nucleophile present in or attached to the protein or peptide, each of A and B independently represents a $C_{1-4}$alkylene or alkenylene chain, and W' represents an electron withdrawing group or a group obtained by reduction of an electron withdrawing group; and in which said polyethylene glycol portion is or includes a pendant polyethylene glycol chain which has a terminal end group of formula —$CH_2CH_2OR$ in which R represents a hydrogen atom, an alkyl group, for example a $C_{1-4}$alkyl group, especially a methyl group, or an optionally substituted aryl group, especially a phenyl group, especially an unsubstituted phenyl group.

The invention also provides a conjugating reagent capable of reacting with a protein or peptide, and including a therapeutic, diagnostic or labelling agent and a polyethylene glycol portion; said conjugating reagent including a group of the formula:

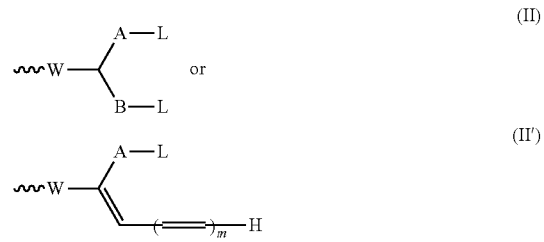

in which W represents an electron withdrawing group, A and B have the meanings given above, m is 0 to 4, and each L independently represents a leaving group; and in which said polyethylene glycol portion is or includes a pendant polyethylene glycol chain which has a terminal end group of formula —$CH_2CH_2OR$ in which R represents a hydrogen atom, an alkyl group, for example a $C_{1-4}$alkyl group, especially a methyl group, or an optionally substituted aryl group, especially a phenyl group, especially an unsubstituted phenyl group.

The invention also provides a process for the preparation of a conjugate according to the invention, which comprises reacting a protein or peptide with a conjugating reagent according to the invention.

The conjugate of the invention may be represented schematically by the formula:

(III)

in which D represents the therapeutic, diagnostic or labelling agent, F' represents the group of formula I, and PEG represents the pendant polyethylene glycol chain having a terminal end group of formula —$CH_2CH_2OR$.

The reagent of the invention may be represented schematically by the formula:

(IV)

in which D represents the therapeutic, diagnostic or labelling agent, F represents the group of formula II or II', and PEG represents the pendant polyethylene glycol chain having a terminal end group of formula —$CH_2CH_2OR$. The functional grouping F is capable of reacting with two nucleophiles present in a protein or peptide as explained below.

A polyethylene glycol (PEG) portion of the conjugates and reagents of the invention is or includes a pendant PEG chain which has a terminal end group of formula —CH$_2$CH$_2$OR in which R represents a hydrogen atom, an alkyl group, for example a C$_{1-4}$alkyl group, especially a methyl group, or an optionally substituted aryl group, especially a phenyl group, especially an unsubstituted phenyl group. Preferably R is a methyl group or a hydrogen atom.

The overall size of the PEG portion will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 g/mole to around 75,000. However, smaller PEG portions may be preferred for some applications.

In one preferred embodiment, all of the PEG in the PEG portion is present in the pendant PEG chain. In another embodiment, PEG may also be present in the backbone of the molecule, and this is discussed in more detail below.

As with the PEG portion, the size of the pendant PEG chain will depend on the intended application. For some applications, high molecular weight pendant PEG chains may be used, for example the number average molecular weight may be up to around 75,000, for example up to 50,000, 40,000 or 30,000 g/mole. For example, the number average molecular weight may be in the range of from 500 g/mole to around 75,000. However, for many applications, smaller pendant PEG chains may be used. For example said PEG chain may have a molecular weight up to 3,000 g/mole. However, very small oligomers, consisting of discrete PEG chains with, for example, as few as 2 repeat units, for example from 2 to 50 repeat units, are useful for some applications, and are present as said PEG chain in one preferred embodiment of the invention. The pendant PEG chain may be straight-chain or branched. PEG chains, for example straight-chain or branched chains with 12, 20, 24, 36, 40 or 48 repeat units may for example be used."

Conjugation Processes

Conjugating reagents containing a functional group capable of reacting with the antibody or antigen-binding portion thereof according to the invention may be reacted with the antibody or antigen-binding portion to form a conjugate, and such a reaction forms a further aspect of the invention. In a preferred embodiment of this further aspect of the invention, a conjugating reagent having one of the structures CI, CI', CII or CIII described above (including all of the preferred sub-structures) is reacted with the antibody or antigen-binding portion thereof to form a conjugate. The immediate product of the conjugation process using one of these reagents is a conjugate which contains an electron-withdrawing group W. However, the conjugation process is reversible under suitable conditions. This may be desirable for some applications, for example where rapid release of the payload is required, but for other applications, rapid release of the payload may be undesirable. It may therefore be desirable to stabilise the conjugates by reduction of the electron-withdrawing moiety W to give a moiety which prevents release of the payload. Accordingly, the process described above may comprise an additional optional step of reducing the electron withdrawing group W in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Thus, for example, a moiety W containing a keto group may be reduced to a moiety containing a CH(OH) group; an ether group may be obtained by the reaction of a hydroxy group with an etherifying agent; an ester group may be obtained by the reaction of a hydroxy group with an acylating agent; an amine group may be prepared from a ketone by reductive amination; or an amide may be formed by acylation of an amine. A sulfone may be reduced to a sulfoxide, sulfide or thiol ether. A cyano group may be reduced to an amine group.

A key feature of using conjugating reagents of formula CI or CII described above is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred to give a reagent of formula CI' and bis-alkylation results from sequential and interactive Michael and retro-Michael reactions. The cross-functional alkylating agents may contain multiple bonds conjugated to the double bond or between the leaving group and the electron withdrawing group.

Where bonding to the antibody or antigen-binding portion thereof is via two sulfur atoms derived from a disulfide bond in the antibody or antigen-binding portion, the process may be carried out by reducing the disulfide bond in situ following which the reduced product reacts with the conjugating reagent having one of the structures C described above. Preferably the disulfide bond is reduced and any excess reducing agent is removed, for example by buffer exchange, before the conjugating reagent is introduced. The disulfide bond can be reduced, for example, with dithiothreitol, mercaptoethanol, or tris-carboxyethylphosphine using conventional methods.

Conjugation reactions may be carried out under similar conditions to known conjugation processes, including the conditions disclosed in the prior art. For example, when using conjugating reagents having one of the structures C described above, the conjugation reaction according to the invention may be carried out under reaction conditions similar to those described in WO 2005/007197, WO 2009/047500, WO2010/100430, WO 2014/064423 and WO 2014/064424. The process may for example be carried out in a solvent or solvent mixture in which all reactants are soluble. For example, the protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone, acetonitrile, DMF, DMSO) are typically conducted at temperatures up to ambient. In one preferred embodiment, the reaction is carried out in aqueous buffer which may contain a proportion of organic solvent, for example up to 20% by volume of organic solvent, typically from 5 to 20% by volume organic solvent.

The antibody or antigen-binding portion can be effectively conjugated using a stoichiometric equivalent or a slight excess of conjugating reagent. However, it is also possible to conduct the conjugation reaction with an excess of conjugating reagent, and this may be desirable for some proteins. The excess reagent can easily be removed by conventional means, for example ion exchange or HPLC chromatography, during subsequent purification of the conjugate.

Of course, it is possible for more than one conjugating reagent to be conjugated to the antibody or antigen-binding portion, where the antibody contains sufficient suitable attachment points. For example, in an antibody which contains two different disulfide bonds, or in an antibody which contains one disulfide bond and also carries a polyhistidine tag, it is possible to conjugate two molecules of the reagent per molecule of antibody. Antibodies generally contain 4 suitable disulfide bonds, and it is possible by a suitable choice of reaction conditions to conjugate one linker carrying a payload across each disulfide bond. If each linker carries a single payload, this give a conjugate with a drug antibody ratio (DAR) of 4. Additional copies of the payload may be attached by use of branched linkers as described above.

When the antibody or antigen-binding fragment thereof is conjugated to a radioactive metal or paramagnetic ion, then in some embodiments, the radioactive metal or paramagnetic ion can be reacted with a reagent having a long tail with one or more chelating groups attached to the long tail for binding these ions. In some embodiments the reagent may carry a reactive group designed to covalently tether the antibody or antigen-binding portion thereof. The long tail can be a polymer such as a polylysine, polysaccharide, polyethylene glycol (PEG) or other derivatised or derivatisable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NODAGA, NETA, deferoxamine (Df, which may also be referred to as DFO), porphyrins, polyamines, crown ethers, bis-thiosemicarbazones, polyoximes, and like groups. The same chelates, when complexed with non-radioactive metals, such as manganese, iron and gadolinium are useful for MRI, when used along with the antibody or antigen-binding portion thereof and carriers described herein. Macrocyclic chelates such as NOTA, NODAGA, DOTA, and TETA are of use with a variety of metals and radiometals including, but not limited to, radionuclides of gallium, yttrium and copper, respectively. Other ring-type chelates such as macrocyclic polyethers, which are of interest for stably binding radionuclides, such as Radium-223 for radioactive immunotherapy (RAIT) may be used. In certain embodiments, chelating moieties may be used to attach a PET (positron emission computed tomography) imaging agent, such as an Aluminum-$^{18}$F or Zirconium-89 complex, to a targeting molecule for use in PET analysis.

Utility and Compositions

The antibodies and antigen-binding portions thereof of the invention, and the conjugates of the invention, find use in the treatment, prevention or diagnosis of diseases and conditions mediated by PSMA or characterised by increased expression of PSMA. The invention therefore provides an antibody or an antigen-binding portion thereof of the invention or a conjugate of the invention for use in diagnosis or therapy, specifically, for use in diagnosing, treating or preventing a disease or condition mediated by PSMA or characterised by increased expression of PSMA. The invention also provides a method of treating or preventing a disease or condition mediated by PSMA or characterised by increased expression of PSMA comprising administering an antibody or antigen-binding portion thereof or a conjugate of the invention to a subject in need thereof in an amount effective to treat or prevent the disease or condition. The invention also provides the use of an antibody or an antigen-binding portion thereof or a conjugate according to the invention for use in the manufacture of a medicament for diagnosing, treating or preventing a disease or condition mediated by PSMA or characterised by increased expression of PSMA.

In some embodiments, the PSMA-mediated disease is a cancer, such as prostate cancer or a non-prostate cancer (including the nonprostate cancers described elsewhere herein). A non-prostate cancer preferably is selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; liver cancer, including metastatic adenocarcinoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma. The most effective cancer treatments generally require the co-administration of several drugs. It is thus preferred for the active agent of the invention to be administered in combination with at least one further chemotherapeutic agent.

In yet another aspect, the present invention provides a method of using antibodies or antigen-binding portions thereof or conjugates of the invention for detecting in vitro or in vivo the presence of PSMA antigen in a sample, e.g., for diagnosing a PSMA-related disease (for example a human PSMA-related disease). In some methods, this is achieved by contacting a sample to be tested, along with a control sample, with an antibody of the invention or an antigen-binding portion thereof or a conjugate of the invention (including a bispecific or multispecific molecule), under conditions that allow for formation of a complex between the antibody and PSMA. Such an assay can be carried out in vitro. Complex formation is then detected (e.g., by ELISA) in the test samples, and any statistically significant increase in the formation of complexes between the test and control samples is indicative of the presence of PSMA in the test sample.

In other embodiments, the present invention can be used in a method of diagnosing a disease or condition mediated by PSMA or characterised by increased expression of PSMA, comprising administering an antibody or antigen-binding portion thereof or a conjugate of the invention conjugated to a diagnostic agent to a subject having or suspected of having a disease or condition mediated by PSMA or characterised by increased expression of PSMA; exposing the subject to an imaging method to visualise the labelled antibody or antigen-binding portion thereof or the conjugate, and determining that the subject has a disease or condition mediated by PSMA or characterised by increased expression of PSMA.

For in vivo diagnostic purposes, an antibody or antigen-binding portion thereof of the invention is preferably in the form of a conjugate in which the antibody is labelled with a detectable marker as described above. Detectable markers include radioactive or fluorescent markers. Radiolabels that can be used on the antibody or antigen-binding antibody fragment to be administered include for example actinium ($^{225}$Ac), astatine ($^{211}$At), bismuth ($^{213}$Bi or $^{212}$Bi), carbon ($^{14}$C), cobalt ($^{57}$Co), copper ($^{67}$Cu), fluorine ($^{18}$F), gallium ($^{68}$Ga or $^{67}$Ga), holmium ($^{166}$Ho), indium ($^{115}$In, $^{113}$In, $^{112}$In, or $^{111}$In), iodine ($^{131}$I, $^{125}$I, $^{123}$I, or $^{121}$I), lead ($^{212}$Pb), lutetium ($^{177}$Lu), palladium ($^{103}$Pd), phosphorous ($^{32}$P), platinum ($^{195}$Pt), rhenium ($^{186}$Re or $^{188}$Re), rhodium ($^{105}$Rh) ruthenium ($^{97}$Ru), samarium ($^{153}$Sm), scandium ($^{47}$Sc), technetium ($^{99}$Tc), ytterbium ($^{169}$Yb or $^{175}$Yb), or yttrium ($^{90}$Y). Fluorescent markers suitable for use with antibodies and antibody fragments are also well known in the art.

When labelled with an appropriate radionuclides (e.g., the positron emitter Iodine-124, Copper-64, Fluorine-18, Gallium-68 and/or Zirconium-89 for PET imaging) or fluorophore (for fluorescent imaging), the antibody or antigen-binding portion thereof can be used for preclinical imaging and/or for clinical imaging in patients. The antibody or antigen-binding portion thereof can also be used as potential SPECT (single photon emission computed tomography) imaging agents by simply changing the radiolabel to single photon emitting radionuclides such as Indium-111, Iodine-123 and Lutitium-177.

In another aspect, the present invention provides a pharmaceutical or diagnostic composition which comprises an antibody or an antigen-binding portion thereof according to the invention, or a conjugate according to the invention, together with a pharmaceutically acceptable carrier. The composition may also if desired contain an additional active ingredient.

EXAMPLES

Commercially available reagents referred to in the Examples were used according to manufacturer's instructions unless otherwise indicated. The source of cells within the Examples and throughout the specification is on each occasion identified either by ECACC or ATCC accession numbers. ECACC is the European Collection of Cell Cultures, Salisbury, England, whereas ATCC is the American Type Culture Collection, Manassas, USA. Unless otherwise defined, all technical and scientific terms used herein have the same meaning as commonly understood by one of ordinary skill in the art to which this invention belongs. Exemplary methods and materials are described below although methods and materials similar or equivalent to those described herein can also be used in the practice or testing of the present invention. The materials, methods, and examples are illustrative only and not intended to be limiting in scope.

| List of Abbreviations | |
| --- | --- |
| Abbreviation | Description |
| 2TYAG | 2x TY broth containing ampicillin (100 μg/ml) and glucose at the specified percentage |
| 2TYAK | 2x TY broth containing ampicillin (100 μg/ml) and kanamycin (50 μg/ml) |
| CD40L | CD40 ligand |
| CDR | Complementarity determining region of an antibody, numbered 1 to 3 per variable region |
| CMV | Cytomegalovirus |
| Ec$_{(0.1\%)}$ | Absorbance of a 1 mg/ml solution of protein |

| List of Abbreviations | |
| --- | --- |
| Abbreviation | Description |
| ELISA | Enzyme-Linked ImmunoSorbent Assay |
| FW | Framework region of an antibody variable region |
| HBS-EP+ | HEPES buffered saline containing 3 mM EDTA and 0.05% v/v Surfactant P20 |
| IC$_{50}$ | Concentration of test antibody that inhibits competitor binding by 50% |
| IgG | Immunoglobulin G |
| IPTG | Isopropyl β-D-1-thiogalactopyranoside |
| k$_a$ | Association rate constant |
| k$_d$ | Dissociation rate constant |
| K$_D$ | Dissociation constant (k$_d$/k$_a$) |
| MHC | Major histocompatibility complex |
| M$_W$ | Molecular weight |
| OD$_{280\,nm}$ | Optical density measured at 280 nm |
| PBS | Phosphate-buffered saline |
| PBSM | Phosphate-buffered saline with 3% w/v Marvel milk powder |
| PBST | Phosphate buffered saline with 0.05% v/v Tween-20 |
| PCR | Polymerase chain reaction |
| R$_{max}$ | Analyte binding level in RUs |
| RU | Resonance units |
| scFv | Single chain variable fragment |
| SDS-PAGE | Sodium dodecyl sulphate polyacrylamide gel electrophoresis |
| S$_m$ | Binding stoichiometry |
| TES | 200 mM Tris HCl pH 8.0,, 0.5 mM EDTA, 0.5M Sucrose |
| TMB | 3,3',5,5'-Tetramethylbenzidine |
| V region | Variable region of an antibody chain |
| VH | Heavy chain variable region |
| Vκ | Kappa light chain variable region |

Example 1: Expression and Purification of Antibodies

Figure 1B:
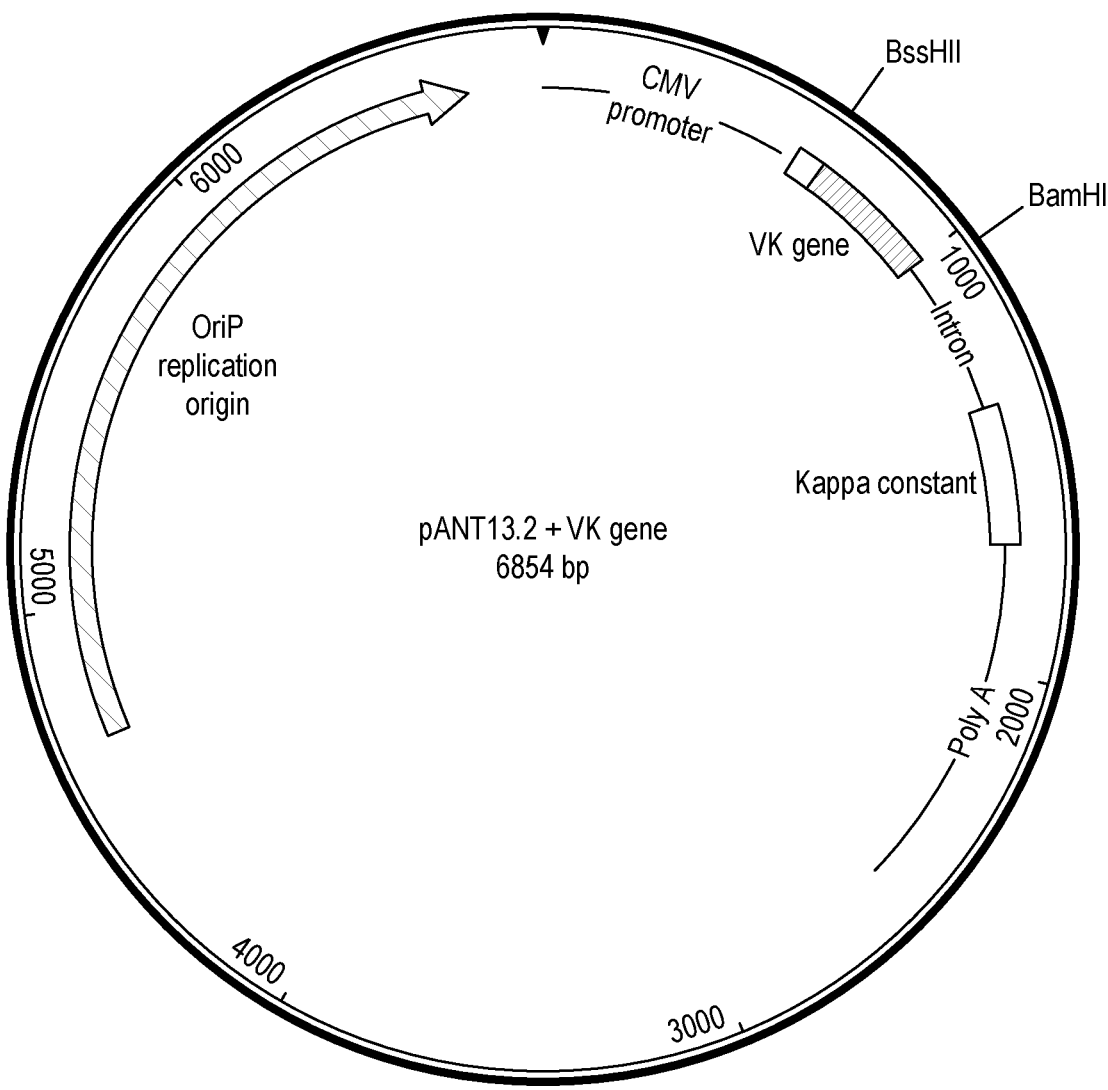
FIG. 1(b) shows the structure of the pANT expression vector for the light chain variable domain (pANT13.2).

The VH and Vκ variants and comparator prior art antibody sequences were subcloned into the pANT expression vectors, pANT17.2 and pANT13.2 for IgG1 heavy chains and for kappa (Km3) light chains, respectively (FIG. 1). VH and Vκ sequences were PCR amplified using primers that introduced flanking restriction enzyme sites for cloning. The VH regions were cloned using MluI and HindIII sites in frame with the human γ1 heavy chain gene (G1m3 (G1m(f)) allotype), and the Vκ regions were cloned using BssHII and BamHI restriction sites in frame with the human kappa light chain constant region gene (Km3 allotype). Transcription of both heavy and light chain genes was under the control of the CMV I/E promoter and the pANT17 plasmid contained a mutant dhfr minigene, under the control of a SV40 promoter, and polyA sequence for selection in eukaryotic cells. All constructs were confirmed by sequencing. Both pANT17.2 and pANT13.2 contained a β-lactamase (Ap$^R$) gene for prokaryotic selection and a pMB1 origin of replication for propagation in prokaryotic cells. All plasmids were propagated in E. coli XL1-blue (Stratagene).

Four heavy chains (designated SEQ ID No 5, 7, 9 and 11) and three light chain sequences (designated SEQ ID No 6, 8 and 10) were selected. The VH variant DNAs were combined with the Vκ variant DNAs. These combinations were transiently transfected into HEK EBNA adherent cells (ATCC®, CRL-10852™) using a PEI transfection method and incubated for 5-7 days post-transfection. Supernatants were used for single cycle SPR analysis or antibodies were purified from cell culture supernatants on Protein A sepharose columns (GE Healthcare), buffer exchanged into PBS pH 7.2 and quantified by OD$_{280nm}$ using an extinction coefficient based on the predicted amino acid sequence. The antibodies that were prepared are shown in Table 1:

TABLE 1

| Antibody Name | Heavy chain | Light chain |
| --- | --- | --- |
| Parent/Template AB-01 | SEQ ID No 12 | SEQ ID No 6 |
| AB-02 | SEQ ID No 5 | SEQ ID No 6 |
| AB-03 | SEQ ID No 7 | SEQ ID No 8 |
| AB-04 | SEQ ID No 9 | SEQ ID No 8 |
| AB-05 | SEQ ID No 5 | SEQ ID No 10 |
| AB-06 | SEQ ID No 11 | SEQ ID No 10 |
| AB-07 | SEQ ID No 12 | SEQ ID No 10 |
| AB-08 | SEQ ID No 13 | SEQ ID No 14 |
| AB-09 | SEQ ID No 15 | SEQ ID No 16 |
| Deimmunised J591 AB-10 | SEQ ID No 3 | SEQ ID No 4 |

Antibodies AB-08, AB-09 and AB-10 are antibodies of the prior art. The Murine J591antibody has heavy chain amino acid SEQ ID No 1 and light chain amino acid SEQ ID No 2. The sequences are shown aligned with each other in FIG. 5.

The DNA sequences used for the expression of the various antibody chains are shown in FIG. 4.

Example 2: Analysis of Antibodies by Competition FACS ELISA

Figure 2:
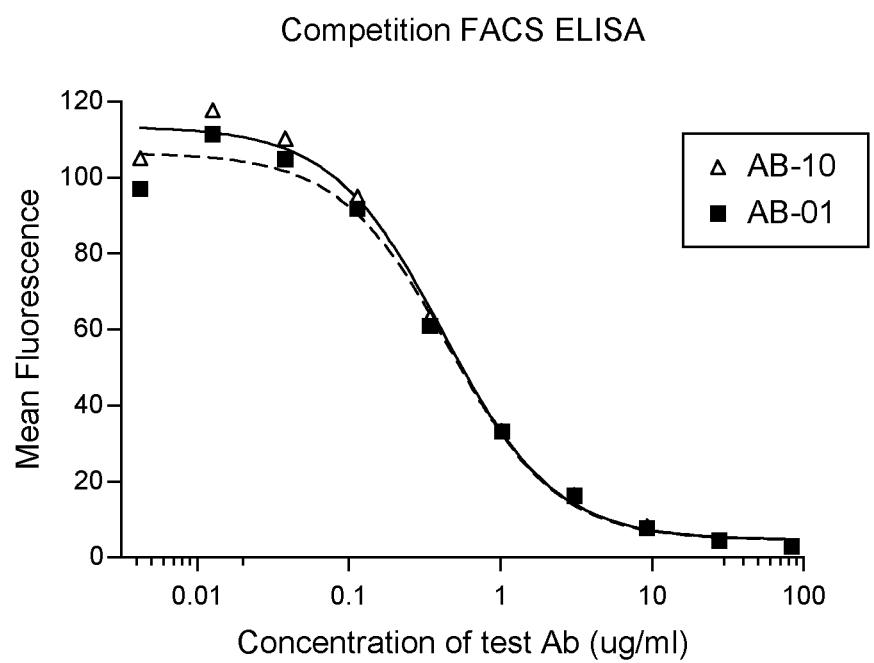
FIG. 2 shows a comparison of competitive binding of AB-01 versus prior art antibody AB-10 to PSMA antigen as analysed by FACS.

The binding of J591 variants to PSMA antigen was assessed in a competition FACS ELISA against the deimmunised J591 reference antibody (AB-10). The AB-10 antibody was fluorescently labelled using the AlexaFluor 488 antibody labelling kit (Molecular Probes, Paisley, UK). PSMA expressing NS0 cells (Clone 6/2F4, $3\times10^5$ cells per staining) were harvested, washed once with Dulbecco's PBS (PAA Laboratories, Yeovil, UK), resuspended in blocking buffer (PBS containing 1% BSA/0.05% sodium azide, 2.5% goat serum) and incubated at room temperature for 30 minutes. Test humanised antibodies at various concentrations were premixed with a constant concentration of Alexafluor 488 labelled AB-10 antibody (0.5 µg/mL final concentration). Blocked cells were then resuspended in 150 µL/well of the pre-diluted antibody mixes and incubated on ice for 1 hour. Following incubation, cells were washed 2× with PBS containing 1% BSA/0.05% sodium azide, transferred to FACS tubes and analysed on a Becton Dickinson (Becton Dickinson, Oxford, UK) FACScalibur instrument, collecting 15000 events per tube. Data was analysed by plotting the geometric mean fluorescence intensity against test antibody concentration. As shown in FIG. 2, AB-01 displays a very similar binding profile to the AB-10, with IC50s of 0.46 and 0.42 ug/ml respectively.

Example 3: Measurement of Affinity Matured Antibodies by Biacore

Kinetic experiments were performed on a Biacore T200, running Biacore T200 Evaluation Software V2.0.1. All experiments were run at 25° C. with HBS-EP+ running buffer (Hepes Buffered Saline+3 mM EDTA and 0.05% (v/v) Surfactant P20, pH 7.4) (GE Healthcare).

All kinetic experiments were performed using recombinant human PSMA (R&D Systems) as the analyte. For all experiments antibodies were immobilised onto a Series S Protein A sensor chip (GE Healthcare) surface. For kinetic experiments, the amount of immobilised/captured ligand needs to be limited to avoid mass transfer effects at the surface of the chip and the surface should ideally have an analyte binding level ($R_{max}$) of 50-150 RUs. Using a MW of 80 kDa for the PSMA analyte, 150 kDa for the antibody ligand (estimated value for IgG), 50 RU for $R_{max}$ and the stoichiometry ($S_m$) as 2 due to the ability of each antibody to bind 2 target molecules, a target response level of ~50 RUs was set for capture of all the sample antibodies.

Single Cycle Analysis

Single cycle kinetic analysis was performed on the supernatants of transiently transfected HEK EBNA cells. Antibodies were diluted in HBS-EP+ to a concentration of 0.5 µg/ml (as determined by an IgG quantitation ELISA). At the start of each cycle, antibodies were loaded onto $F_c2$, $F_c3$ and $F_c4$ of a protein A chip and IgG captured at a flow rate of 10 µl/min to give an RU of ~50. The surface was then allowed to stabilise. Single cycle kinetic data was obtained at a flow rate of 40 µl/min to minimise any potential mass transfer effects. Multiple repeats of the AB-01 antibody were performed to check the stability of the surface and analyte over the kinetic cycles. The signal from the reference channel $F_c1$ (no antibody) was subtracted from that of $F_c2$, $F_c3$ and FA to correct for differences in non-specific binding to a reference surface. A 3 point 2-fold dilution range from 12.5 to 50 nM PSMA without regeneration between each concentration was used. The association phase for the 3 injections of increasing concentrations of PSMA was monitored for 200 seconds and a single dissociation phase was measured for 300 seconds following the last injection of PSMA. Regeneration of the Protein A surface was conducted using 2 injections of 10 mM glycine-HCL, pH 1.5, followed by a stabilisation period of 400 seconds.

Multi-Cycle Analysis

For multi-cycle kinetic analysis, purified antibody was immobilised at a protein concentration of 0.5 µg/ml in HBS-EP+. At the start of each cycle, antibody was captured on Protein A to give an RU of ~50 and the surface allowed to stabilise. Kinetic data was obtained at a flow rate of 35 µl/min to minimise any potential mass transfer effects. Multiple repeats of the blank (no PSMA) and a repeat of a single concentration of the analyte were programmed into the kinetic run in order to check the stability of both the surface and analyte over the kinetic cycles. For kinetic analysis, a 2-fold dilution range was selected from 100 to 3.125 nM PSMA. The association phase of PSMA was monitored for 600 seconds and the dissociation phase was measured for 1200 seconds. Regeneration of the Protein A surface was conducted using 2 injections of 10 mM glycine-HCL pH 1.5 at the end of each cycle.

The signal from the reference channel $F_c1$ was subtracted from that of $F_c2$, $F_c3$ and $F_c4$ to correct for differences in non-specific binding to a reference surface, a global $R_{max}$ parameter was used in the 1-to-1 binding model. The relative $K_D$ compared to AB-01 mAb was calculated by dividing the $K_D$ of the variants by that of AB-01 mAb on the same chip.

TABLE 2a

| Antibody Name | KD (M) | Relative KD |
| --- | --- | --- |
| AB-01 | 5.53E−10 | 1.00 |
| AB-02 | 2.80E−10 | 1.98 |
| AB-04 | 3.54E−10 | 1.56 |

TABLE 2b

| Antibody Name | KD (M) | Relative KD |
| --- | --- | --- |
| AB-01 | 4.45E−10 | 1.00 |
| AB-03 | 2.45E−10 | 1.82 |

TABLE 2c

| Antibody Name | KD (M) | Relative KD |
| --- | --- | --- |
| AB-01 | 4.13E−10 | 1.00 |
| AB-05 | 2.24E−10 | 1.84 |

TABLE 2d

| Antibody Name | KD (M) | Relative KD |
| --- | --- | --- |
| AB-01 | 5.05E−10 | 1.00 |
| AB-06 | 3.42E−10 | 1.48 |

TABLE 2e

| Antibody Name | KD (M) | Relative KD |
| --- | --- | --- |
| AB-01 | 4.69E−10 | 1.00 |
| AB-07 | 3.58E−10 | 1.31 |

The data shown in Tables 2a to 2e show that each of these antibodies possesses better affinity for the PSMA antigen than the AB-01 antibody as analysed using Biacore analysis. As the AB-01 antibody has essentially the same affinity for the PSMA antigen as the known de-immunised J591 antibody (herein AB-10, see Example 2 above), it is seen that the antibodies of the current invention have better affinity for the PSMA antigen than J591 antibodies of the prior art.

Example 4: Comparison of the Stability of Anti-PSMA Antibodies by Heat Stress Test Antibody samples (0.5 mg/mL in PBS) were incubated at 75° C. for 30 min followed by incubation in an ice-bath for 5 min prior to being analysed for their extent of aggregation. Analysis of antibody solutions was carried out by Size Exclusion Chromatography (SEC) and by turbidity measurements.
SEC:
SEC was performed using a TOSOH Bioscience TSK gel Super SW 3000 column. UV absorbance at 280 nm was monitored during an isocratic elution with a 0.2 M Potassium phosphate buffer, pH 6.8 (0.2 M potassium chloride and 15% isopropanol). The elution times and number of peaks indicate whether the sample contains aggregated, degraded or native antibody. The % area under the curve (Abs280) was used to determine the quantity of each species present in the SEC analysis.
Results:
The results of the stability assay are shown in Table 3. From this analysis, it can be seen that prior art antibodies AB-08, AB-09 and AB-10 are less stable than the AB-02 to AB-06 antibodies of the current invention.

TABLE 3

| Antibody analysis- post stress test. | Ab in native conformation (%) | Ab in aggregated form (%) |
| --- | --- | --- |
| AB-02 | 10 | 90 |
| AB-03 | 36 | 64 |
| AB-04 | 27 | 73 |
| AB-05 | 2 | 98 |
| AB-06 | 2 | 98 |
| Deimmunised J591 AB-10 | 0.4 | 99.6 |
| AB-08 | 0 | 100 |
| AB-09 | 0 | 100 |

Example 5: Conjugation of Anti-PSMA Antibodies with the Maleimide Reagent Mc-Vc-PAB-MMAE to Produce Conjugates Anti-PSMA antibodies, AB-02, AB-03, AB-04, AB-05, AB-06, AB-08 and AB-09 were conjugated as described below to produce conjugates 1, 2, 3, 4, 5, 6 and 7 respectively.

Anti-PSMA antibodies each at a concentration of 5.2 mg/mL in reaction buffer (20 mM sodium phosphate, 150 mM NaCl, 20 mM EDTA, pH 7.5), were heated to 40° C. for 15 min. TCEP (2 eq.) was added to each mAb solution, mixed gently and incubated at 40° C. for 1 h before being allowed to cool to 22° C. The maleimide reagent, mc-val-cit-PAB-MMAE (Concortis Biosystems), was dissolved in DMF to give a 2.1 mM stock solution. The reduced mAb solutions were diluted to 4.2 mg/mL with reaction buffer, mc-val-cit-PAB-MMAE (4 eq. per mAb) was added and the reaction was mixed gently and incubated at 22° C. for 1.5 h. The reactions were finally treated with 50 mM N-acetyl-L-cysteine (20 eq. over reagent) and incubated at 22° C. for 1 h. The crude conjugation mixtures were analysed by hydrophobic interaction chromatography. The crude reactions were diafiltered (Vivaspin 6, 30 kDa PES membrane) against DPBS, pH 7.1-7.5 to remove reactants and concentrate the conjugates. The concentrated samples were buffer exchanged into DPBS, pH 7.1-7.5 by gel filtration and then sterile filtered (0.22 µm PVDF membranes).

Purified conjugates were analysed by hydrophobic interaction chromatography (HIC) using a TOSOH TSK-gel Butyl-NPR column. The area of each peak obtained for each drug to antibody ratio (DAR) variant, (identified by the ratio of the UV absorbance maxima for drug (248 nm) and antibody (280 nm) and order of peak elution) was analysed. The average DAR was calculated by taking the sum of the integrated area of each DAR variant multiplied by the DAR and dividing this value by the total integrated area. The average DAR values obtained for each conjugation were 3.5 (±0.2).

Example 6: Analysis of Antibody Drug Conjugates and Free Payload by In Vitro Cell Viability Assay The in vitro efficacies of ADCs 1 to 7, prepared as described within Example 4, were determined by measuring their inhibitory effect upon cell growth of PSMA over-expressing cancer cell lines.

Loss of tumour cell viability following treatment with cytotoxic drugs or ADCs in vitro can be measured by growing cell lines in the presence of increasing concentrations of drugs or ADCs and quantifying the loss of proliferation or metabolic activity using CellTiter Glo® Luminescence reagent (Promega Corp.). The protocol describes cell seeding, drug treatment and determination of the cell viability in reference to untreated cells based on ATP synthesis, which is directly related to the number of cells present in the well.

Tumour cell lines LNCaP (CRL-1740) were purchased from the American Type Culture Collection (ATCC). LNCaP and C4-2 cells were grown in RPMI-1640 medium containing 2 mM glutamine (Life Technologies®), 10% fetal bovine serum, 100 U/mL Penicillin and 100 µg/mL Streptomycin. The cells were maintained as described in the product information sheets and following ATCC general recommendations for tissue culture. Cells were cultured according to ATCC recommendations and references quoted therein, for example, Culture of Animal Cells: A Manual of Basic Technique by R. Ian Freshney 3rd edition, published by Alan R. Liss, N.Y. 1994, or 5th edition published by Wiley-Liss, N.Y. 2005.

The cell viability assay was carried out using the Cell-Titer Glo® Luminescence reagent, as described by the manufacturer's instructions, (Promega Corp. Technical Bulletin TB288; Lewis Phillips G. D, Cancer Res 2008; 68:9280-9290). Luminescence was recorded using a plate reader (e.g. Molecular Devices Spectramax M3 plate reader), and data subsequently analysed using a four parameter non-linear regression model.

If plotted as a graph, viability was expressed as % of untreated cells and calculated using the following formula:

$$\% \text{ Viability} = 100 \times \frac{\text{Luminescence}_{Sample} - \text{Luminescence}_{No\,cell\,Control}}{\text{Luminescence}_{Untreated} - \text{Luminescence}_{No\,cell\,Control}}$$

The % viability (Y-axis) was plotted against the logarithm of drug concentration in nM (X-axis) to extrapolate the IC50 values for all conjugates as well as free drugs.

PSMA-positive LNCaP (clone FGC) and C4-2 cells were detached with TrypLE and resuspended in complete medium. Cells were counted using disposable Neubauer counting chambers and cell density adjusted to $10 \times 10^4$ cells/mL for LNCaP and $2 \times 10^4$ cells/mL for C4-2. Cells were seeded (100 µL/well) into either Tissue Culture treated (C4-2) or Poly-D-Lysine coated (LNCaP), white, opaque-walled, 96-well plates and incubated for 24 h at 37° C. and 5% $CO_2$ prior to assay.

Eight point serial dilutions of ADCs or free drug were prepared in triplicate in the relevant culture medium. Cell lines were treated with ADC concentrations of 50-0.00064 nM. MMAE was used at 500-0.0064 nM on C4-2 cells and 10,000-0.128 nM on LNCaP cells. The medium from the plate containing the adherent cells was removed and replaced by 100 µL/well of the serially diluted compounds. The cells were then incubated at 37° C. and 5% $CO_2$ for a further 96 h.

As shown in Table 4, in the concentration range tested, all ADCs were able to specifically inhibit the proliferation of PSMA expressing LNCaP and C4-2 cells.

TABLE 4

$IC_{50}$ values showing the anti-proliferative effect of ADCs and free MMAE payload on LNCaP and C4-2 cells.

| ADC/Drug | LNCaP IC50 (nM) | C4-2 IC50 (nM) |
|---|---|---|
| 1 AB-02-mc-val-cit-PAB-MMAE | 0.61 | 0.18 |
| 2 AB-03-mc-val-cit-PAB-MMAE | 0.70 | 0.22 |
| 3 AB-04-mc-val-cit-PAB-MMAE | 0.67 | 0.21 |
| 4 AB-05-mc-val-cit-PAB-MMAE | 1.27 | 0.41 |
| 5 AB-06-mc-val-cit-PAB-MMAE | 0.78 | 0.26 |
| 6 AB-08-mc-val-cit-PAB-MMAE | 1.03 | 0.31 |
| 7 AB-09-mc-val-cit-PAB-MMAE | 0.89 | 0.24 |
| MMAE | 2.23 | 0.63 |

The invention claimed is:

1. An antibody or antigen-binding portion thereof which binds to PSMA and comprises a heavy chain variable domain and a light chain variable domain, wherein the heavy chain variable domain comprises the sequences:

```
                                     (SEQ ID NO: 33)
        CDR1: EYTIH (SEQ ID NO: 34)
        CDR2: NINPNX¹GGTTYNQKFED; and (SEQ ID NO: 35)
        CDR3: X²⁻⁵DY
``` wherein
$X^1$ is N or Q, and
$X^{2-5}$ is YWLF (SEQ ID NO: 39), GWTF (SEQ ID NO: 40) or AWTM (SEQ ID NO: 41), and wherein
if $X^{2-5}$ is GWTF (SEQ ID NO: 40) or AWTM (SEQ ID NO: 41), the amino acid residue at position H94 in the heavy chain variable region, based on Kabat numbering, is G; and
if $X^{2-5}$ is YWLF (SEQ ID NO: 39), the amino acid residue at position H94 in the heavy chain variable region, based on Kabat numbering, is A; and
wherein the light chain variable domain comprises the sequences:

```
                                     (SEQ ID NO: 36)
        CDR1: KASQDVGTAVD (SEQ ID NO: 37)
        CDR2: WASTRHT; and (SEQ ID NO: 38)
        CDR3: QQX¹⁻⁵LT
``` wherein $X^{1-5}$ is FTRYP or YNAYS.

2. An antibody or antigen-binding portion thereof as claimed in claim 1, which comprises a heavy chain variable domain comprising the sequence given in SEQ ID NO:29, wherein

```
SEQ ID NO: 29 is:
EVQLVQSGAE VKKPGASVKV SCKASGYTFT EYTIHWVRQA

PGKGLEWIGN INPNNGGTTY NQKFEDRVTI TVDKSTSTAY

MELSSLRSED TAVYYCAX⁹⁸X⁹⁹⁻¹⁰²DYWGQGTT VTVSS
``` wherein:
$X^{98-102}$ is AYWLF (SEQ ID NO: 42), GGWTF (SEQ ID NO: 43), or GAWTM (SEQ ID NO: 44),
whereby the heavy chain variable domain comprises up to 12 amino acid sequence modification(s) at any of positions 1-30, 36-49, 67-97 and 105-115 of SEQ ID NO: 29.

3. An antibody or antigen-binding portion thereof as claimed in claim 1, which comprises a heavy chain variable domain comprising the sequence given in SEQ ID NO:30, wherein

```
SEQ ID NO: 30 is:
EVQLVQSGX⁹E X¹¹KKPGASVKV SCKX²⁴SGYTFT EYTIHWVX³⁸QA

X⁴¹GKGLEWIGN INPNX⁵⁵GGTTY NQKFEDRX⁶⁸TX⁷⁰ TVDKSTSTA

YMELSSX⁸⁶RSED TAVYYCAX⁹⁸X⁹⁹X¹⁰⁰ X¹⁰¹X¹⁰² DYWGQGTT

VTVSS
``` wherein:
$X^9$ is A or P
$X^{11}$ is V or L
$X^{24}$ is A or T
$X^{38}$ is R or K
$X^{41}$ is P or H
$X^{55}$ is N or Q
$X^{68}$ is V or A
$X^{70}$ is I or L,
$X^{86}$ is L or P, and
$X^{98-102}$ is AYWLF (SEQ ID NO: 42), GGWTF (SEQ ID NO: 43), or GAWTM (SEQ ID NO: 44),
whereby the heavy chain variable domain comprises up to 3 amino acid sequence modification(s) between positions 1-30, 36-49, 67-98 and 105-115 of SEQ ID NO: 30.

4. An antibody or antigen-binding portion thereof as claimed in claim 3, wherein in SEQ ID NO:30 $X^9$ is A, $X^{11}$ is V, $X^{24}$ is A or T, $X^{38}$ is R or K, $X^{41}$ is P, $X^{55}$ is N or Q, $X^{68}$ is V or A, $X^{70}$ is I and $X^{86}$ is L or P.

5. An antibody or antigen-binding portion thereof as claimed in claim 1, which comprises a light chain variable domain comprising the sequence given in SEQ ID NO:31, wherein

```
SEQ ID NO: 31 is:
DIQMTQSPST LSASVGDRVT ITCKASQDVG TAVDWYQQKP

GQAPKLLIYW ASTRHTGVPD RFSGSGSGTD FTLTISRLQP

EDFAVYYCQQ X⁹¹⁻⁹⁵LTFGQ GTKVDIK
``` wherein
$X^{91-95}$ is FTRYP (SEQ ID NO: 45) or YNAYS (SEQ ID NO: 46),
whereby the light chain variable domain comprises up to 10 amino acid sequence modification(s) between positions 1-23, 35-49, 57-88 and 98-107 of SEQ ID NO: 31.

6. An antibody or antigen-binding portion thereof as claimed in claim 1, which comprises a light chain variable domain comprising the sequence given in SEQ ID NO:32, wherein

```
SEQ ID NO: 32 is:
DIX³MTQSPSX¹⁰ LSASVGDRVT ITCKASQDVG TAVDWYQQKP

GQAPKLLIYW ASTRHTGVPD RFX⁶³GSGSGTD FTLTISRLQX⁸⁰

EDFAX⁸⁵YX⁸⁷CQQ X⁹¹⁻⁹⁵LTFGQ GTX¹⁰³VDIK
``` wherein
$X^3$ is Q or V
$X^{10}$ is T or F
$X^{63}$ is S or T
$X^{80}$ is P or S
$X^{85}$ is V or D
$X^{87}$ is Y or F
$X^{91-95}$ is FTRYP (SEQ ID NO: 45) or YNAYS (SEQ ID NO: 46); and
$X^{103}$ is K or M,
whereby the light chain variable domain comprises up to 3 amino acid sequence modification(s) between positions 1-23, 35-49, 57-88 and 98-107 of SEQ ID NO: 32.

7. An antibody or antigen-binding portion thereof as claimed in claim 6, wherein in SEQ ID NO:32 $X^3$ is Q or V, $X^{10}$ is T, $X^{63}$ is S or T, $X^{80}$ is P or S, $X^{85}$ is V or D, $X^{87}$ is Y or F and $X^{103}$ is K.

8. A polynucleotide encoding an antibody or antigen-binding portion thereof as claimed in claim 1.

9. A vector comprising the polynucleotide as claimed in claim 8.

10. A host cell comprising a vector as claimed in claim 9.

11. An antibody conjugate comprising an antibody or antigen-binding portion thereof as claimed in claim 1 conjugated via a linker to a payload.

12. An antibody conjugate as claimed in claim 11, in which the payload is bonded to the antibody or antigen-binding portion thereof via a bonding portion which has the general formula:

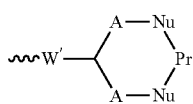
(I)

in which Pr represents said antibody or antigen-binding portion thereof, each Nu represents a nucleophile present in or attached to the antibody or antigen-binding portion thereof, each of A and B independently represents a $C_{1-4}$alkylene or alkenylene chain, and W' represents an electron withdrawing group or a group obtained by reduction of an electron withdrawing group.

13. A conjugate as claimed in claim 12, in which W' is a keto group —CO—.

14. A conjugate as claimed in claim 12, in which the bonding portion has the formula:

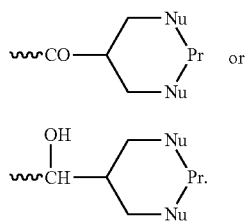
(Ib)

or (Ic)

15. A conjugate as claimed in claim 11, in which the payload is or includes an auristatin or a maytansinoid.

16. A conjugate as claimed in claim 11, which includes from 1 to 20 molecules of a therapeutic agent.

17. A conjugate as claimed in claim 11, which includes a radioisotope.

18. A conjugate as claimed in claim 11, in which the payload is or includes a detectable marker selected from the group consisting of at least one of a radioactive substance, a dye, a contrast agent, a fluorescent compound, a bioluminescent compound, an enzyme, an enhancing agent, and a nanoparticle.

19. A method of diagnosing or treating a disease or condition mediated by PSMA or characterised by increased expression of PSMA comprising administering an antibody or antigen-binding portion thereof as claimed in claim 1, to a subject in need thereof in an amount effective to diagnose or treat the disease or condition.

20. A method for detecting in vitro or in vivo the presence of PSMA antigen in a test sample using an antibody or an antigen-binding portion thereof as claimed in claim 1, said method comprising:

(a) contacting the sample with the antibody or the antigen-binding portion thereof under conditions that allow for formation of a complex between a PSMA antigen and the antibody or the antigen-binding portion thereof;

(b) detecting the presence of the complex.

21. A method of diagnosing or treating a disease or condition mediated by PSMA or characterised by increased expression of PSMA comprising administering an antibody conjugate as claimed in claim 11, to a subject in need thereof in an amount effective to diagnose or treat the disease or condition.

22. A method for detecting in vitro or in vivo the presence of PSMA antigen in a test sample using an antibody conjugate as claimed in claim 11, said method comprising:

(a) contacting the test sample with the antibody conjugate under conditions that allow for formation of a complex between a PSMA antigen and the antibody conjugate;

(b) detecting the presence of the complex.

23. The method of claim 19, wherein the disease mediated by PSMA is cancer.

24. The method of claim 23 wherein the cancer is prostate cancer.

25. The method of claim 23 wherein the cancer is bladder cancer, pancreatic cancer, lung cancer, kidney cancer, sarcoma, liver cancer, breast cancer, brain cancer, colon cancer, testicular cancer, or melanoma.

26. The method of claim 23, wherein the cancer is transitional cell carcinoma of the bladder, pancreatic duct carcinoma, non-small cell lung carcinoma, conventional renal cell carcinoma, soft tissue sarcoma, metastatic adenocarcinoma of the liver, breast carcinoma, glioblastoma multiforme, neuroendocrine carcinoma, colonic carcinoma, testicular embryonal carcinoma, or malignant melanoma.

27. An antibody conjugate comprising an antibody or antigen-binding portion thereof as claimed in claim 1.

28. An antibody or antigen-binding portion thereof as claimed in claim 2, which comprises a light chain variable domain comprising the sequence given in SEQ ID NO:31, wherein

```
                                      SEQ ID NO: 31 is:
DIQMTQSPST LSASVGDRVT ITCKASQDVG TAVDWYQQKP

GQAPKLLIYW ASTRHTGVPD RFSGSGSGTD FTLTISRLQP

EDFAVYYCQQ X⁹¹⁻⁹⁵LTFGQ GTKVDIK
``` wherein $X^{91-95}$ is FTRYP (SEQ ID NO: 45) or YNAYS (SEQ ID NO: 46), whereby the light chain variable domain comprises up to 10 amino acid sequence modification(s) between positions 1-23, 35-49, 57-88 and 98-107 of SEQ ID NO: 31.

29. An antibody or antigen-binding portion thereof as claimed in claim 3, which comprises a light chain variable domain comprising the sequence given in SEQ ID NO:32, wherein

```
                                      SEQ ID NO: 32 is:
DIX³MTQSPSX¹⁰ LSASVGDRVT ITCKASQDVG TAVDWYQQKP

GQAPKLLIYW ASTRHTGVPD RFX⁶³GSGSGTD FTLTISRLQX⁸⁰

EDFAX⁸⁵YX⁸⁷CQQ X⁹¹⁻⁹⁵LTFGQ GTX¹⁰³VDIK
``` wherein $X^3$ is Q or V $X^m$ is T or F $X^{63}$ is S or T $X^{80}$ is P or S $X^{85}$ is V or D $X^{87}$ is Y or F $X^{91-95}$ is FTRYP (SEQ ID NO: 45) or YNAYS (SEQ ID NO: 46); and $X^{103}$ is K or M whereby the light chain variable domain comprises up to 3 amino acid sequence modification(s) between positions 1-23, 35-49, 57-88 and 98-107 of SEQ ID NO: 32.

30. An antibody or antigen-binding portion thereof as claimed in claim 29, wherein in SEQ ID NO:32 $X^3$ is Q or V, $X^{10}$ is T, $X^{63}$ is S or T, $X^{80}$ is P or S, $X^{85}$ is V or D, $X^{87}$ is Y or F and $X^{103}$ is K.

31. A conjugate as claimed in claim 17, wherein the radioisotope is selected from the group consisting of Iodine-131, Yttrium-90, Lutetium-177, Copper-67, Astatine-211, Lead-212/Bismuth-212, Actinium-225/Bismuth-213, and Thorium.

* * * * *

UNITED STATES PATENT AND TRADEMARK OFFICE
CERTIFICATE OF CORRECTION

PATENT NO. : 11,059,903 B2  
APPLICATION NO. : 16/303600  
DATED : July 13, 2021  
INVENTOR(S) : Robert George Edward Holgate et al.

Page 1 of 1

It is certified that error appears in the above-identified patent and that said Letters Patent is hereby corrected as shown below:

In the Specification

At Column 22, Line 15:
Delete "$R^i, R^{ii}, R^{iii}$" and replace with --$R^i, R^{ii}, R^{iii}, R^{iiii}$--

At Column 27, Line 56:

The recitation of " 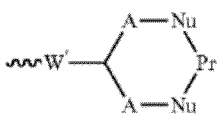 " should read -- 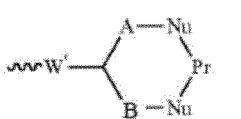 --

In the Claims

At Column 73, Line 20, Claim 12:

The recitation of " 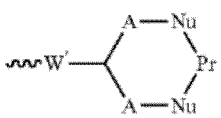 " should read -- 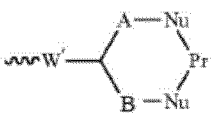 --

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 46

<210> SEQ ID NO 1
<211> LENGTH: 115
<212> TYPE: PRT
<213> ORGANISM: Artificial sequence
<220> FEATURE:
<223> OTHER INFORMATION: synthetic sequence

<400> SEQUENCE: 1

Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
            35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
    115
```

```
<210> SEQ ID NO 2
<211> LENGTH: 107
<212> TYPE: PRT
<213> ORGANISM: Artificial sequence
<220> FEATURE:
<223> OTHER INFORMATION: synthetic sequence

<400> SEQUENCE: 2

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Met Leu Asp Leu Lys
            100                 105

<210> SEQ ID NO 3
<211> LENGTH: 115
<212> TYPE: PRT
<213> ORGANISM: Artificial sequence
<220> FEATURE:
<223> OTHER INFORMATION: synthetic sequence

<400> SEQUENCE: 3

Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
            100                 105                 110

Val Ser Ser
        115

<210> SEQ ID NO 4
<211> LENGTH: 107
<212> TYPE: PRT
<213> ORGANISM: Artificial sequence
<220> FEATURE:
<223> OTHER INFORMATION: synthetic sequence

<400> SEQUENCE: 4

Asp Ile Gln Met Thr Gln Ser Pro Ser Ser Leu Ser Thr Ser Val Gly
1               5                   10                  15

Asp Arg Val Thr Leu Thr Cys Lys Ala Ser Gln Asp Val Gly Thr Ala
            20                  25                  30
```

```
Val Asp Trp Tyr Gln Gln Lys Pro Gly Pro Ser Pro Lys Leu Leu Ile
         35                  40                  45

Tyr Trp Ala Ser Thr Arg His Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Asp Tyr Tyr Cys Gln Gln Tyr Asn Ser Tyr Pro Leu
                 85                  90                  95

Thr Phe Gly Pro Gly Thr Lys Val Asp Ile Lys
            100                 105

<210> SEQ ID NO 5
<211> LENGTH: 115
<212> TYPE: PRT
<213> ORGANISM: Artificial sequence
<220> FEATURE:
<223> OTHER INFORMATION: synthetic sequence

<400> SEQUENCE: 5

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Tyr
                 20                  25                  30

Thr Ile His Trp Val Arg Gln Ala Pro Gly Lys Gly Leu Glu Trp Ile
             35                  40                  45

Gly Asn Ile Asn Pro Asn Asn Gly Gly Thr Thr Tyr Asn Gln Lys Phe
 50                  55                  60

Glu Asp Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Tyr Trp Leu Phe Asp Tyr Trp Gly Gln Gly Thr Thr Val Thr
            100                 105                 110

Val Ser Ser
        115

<210> SEQ ID NO 6
<211> LENGTH: 107
<212> TYPE: PRT
<213> ORGANISM: Artificial sequence
<220> FEATURE:
<223> OTHER INFORMATION: synthetic sequence

<400> SEQUENCE: 6

Asp Ile Gln Met Thr Gln Ser Pro Ser Thr Leu Ser Ala Ser Val Gly
 1               5                  10                  15

Asp Arg Val Thr Ile Thr Cys Lys Ala Ser Gln Asp Val Gly Thr Ala
                 20                  25                  30

Val Asp Trp Tyr Gln Gln Lys Pro Gly Gln Ala Pro Lys Leu Leu Ile
             35                  40                  45

Tyr Trp Ala Ser Thr Arg His Thr Gly Val Pro Asp Arg Phe Ser Gly
 50                  55                  60

Ser Gly Ser Gly Thr Asp Phe Thr Leu Thr Ile Ser Arg Leu Gln Pro
 65                  70                  75                  80

Glu Asp Phe Ala Val Tyr Tyr Cys Gln Gln Tyr Asn Ser Tyr Pro Leu
                 85                  90                  95

Thr Phe Gly Gln Gly Thr Lys Val Asp Ile Lys
            100                 105
```

```
<210> SEQ ID NO 7
<211> LENGTH: 115
<212> TYPE: PRT
<213> ORGANISM: Artificial sequence
<220> FEATURE:
<223> OTHER INFORMATION: synthetic sequence

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Ile His Trp Val Arg Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Trp Thr Phe Asp Tyr Trp Gly Gln Gly Thr Thr Val Thr
            100                 105                 110

Val Ser Ser
        115

<210> SEQ ID NO 8
<211> LENGTH: 107
<212> TYPE: PRT
<213> ORGANISM: Artificial sequence
<220> FEATURE:
<223> OTHER INFORMATION: synthetic sequence

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
                20                  25                  30

Val Asp Trp Tyr Gln Gln Lys Pro Gly Gln Ala Pro Lys Leu Leu Ile
            35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Phe Thr Arg Tyr Pro Leu
                85                  90                  95

Thr Phe Gly Gln Gly Thr Lys Val Asp Ile Lys
            100                 105

<210> SEQ ID NO 9
<211> LENGTH: 115
<212> TYPE: PRT
<213> ORGANISM: Artificial sequence
<220> FEATURE:
<223> OTHER INFORMATION: synthetic sequence

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30
```

```
Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
 50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ala Trp Thr Met Asp Tyr Trp Gly Gln Gly Thr Thr Val Thr
            100                 105                 110

Val Ser Ser
        115

<210> SEQ ID NO 10
<211> LENGTH: 107
<212> TYPE: PRT
<213> ORGANISM: Artificial sequence
<220> FEATURE:
<223> OTHER INFORMATION: synthetic sequence

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
                20                  25                  30

Val Asp Trp Tyr Gln Gln Lys Pro Gly Gln Ala Pro Lys Leu Leu Ile
            35                  40                  45

Tyr Trp Ala Ser Thr Arg His Thr Gly Val Pro Asp Arg Phe Ser Gly
 50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ala Tyr Ser Leu
                85                  90                  95

Thr Phe Gly Gln Gly Thr Lys Val Asp Ile Lys
            100                 105

<210> SEQ ID NO 11
<211> LENGTH: 115
<212> TYPE: PRT
<213> ORGANISM: Artificial sequence
<220> FEATURE:
<223> OTHER INFORMATION: synthetic sequence

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Ile His Trp Val Arg Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
 50                  55                  60

Glu Asp Arg Val Thr Ile Thr Val Asp Lys Ser Thr Ser Thr Ala Tyr
65                  70                  75                  80

Met Glu Leu Ser Ser Pro Arg Ser Glu Asp Thr Ala Val Tyr Tyr Cys
                85                  90                  95
```

```
Ala Ala Gly Trp Asn Phe Asp Tyr Trp Gly Gln Gly Thr Thr Val Thr
                100                 105                 110

Val Ser Ser
        115

<210> SEQ ID NO 12
<211> LENGTH: 115
<212> TYPE: PRT
<213> ORGANISM: Artificial sequence
<220> FEATURE:
<223> OTHER INFORMATION: synthetic sequence

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Ile His Trp Val Arg Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
        50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
                100                 105                 110

Val Ser Ser
        115

<210> SEQ ID NO 13
<211> LENGTH: 142
<212> TYPE: PRT
<213> ORGANISM: Artificial sequence
<220> FEATURE:
<223> OTHER INFORMATION: synthetic sequence

<400> SEQUENCE: 13

Met Glu Leu Gly Leu Arg Trp Gly Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Ala Phe
            35                  40                  45

Ser Arg Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Gln Tyr Leu Gln Met Asn Ser Leu Arg Ala Glu Thr Ala Val
                100                 105                 110

Tyr Tyr Cys Ala Arg Gly Gly Asp Phe Leu Tyr Tyr Tyr Tyr Gly
            115                 120                 125

Met Asp Val Trp Gly Gln Gly Thr Thr Val Thr Val Ser Ser
        130                 135                 140
```

-continued

```
<210> SEQ ID NO 14
<211> LENGTH: 127
<212> TYPE: PRT
<213> ORGANISM: Artificial sequence
<220> FEATURE:
<223> OTHER INFORMATION: synthetic sequence

<400> SEQUENCE: 14

Met Arg Val Pro Ala Gln Leu Leu Gly Leu Leu Leu Trp Leu Pro
1               5                   10                  15

Asp Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Asn Tyr Leu Ala Trp Tyr Gln Gln Lys Thr Gly Lys Val Pro
    50                  55                  60

Lys Phe Leu Ile Tyr Glu Ala Ser Thr Leu Gln Ser Gly Val Pro Ser
65                  70                  75                  80

Arg Phe Ser Gly Gly Gly Ser Gly Thr Asp Phe Thr Leu Thr Ile Ser
                85                  90                  95

Ser Leu Gln Pro Glu Asp Val Ala Thr Tyr Tyr Cys Gln Asn Tyr Asn
            100                 105                 110

Ser Ala Pro Phe Thr Phe Gly Pro Gly Thr Lys Val Asp Ile Lys
        115                 120                 125

<210> SEQ ID NO 15
<211> LENGTH: 143
<212> TYPE: PRT
<213> ORGANISM: Artificial sequence
<220> FEATURE:
<223> OTHER INFORMATION: synthetic sequence

<400> SEQUENCE: 15

Met Glu Leu Gly Leu Arg Trp Val Leu Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Ala Pro Gly Lys Gly Leu
    50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Gly Gly Tyr Asn Trp Asn Tyr Glu Tyr His Tyr Tyr
        115                 120                 125

Gly Met Asp Val Trp Gly Gln Gly Thr Thr Val Thr Val Ser Ser
    130                 135                 140

<210> SEQ ID NO 16
<211> LENGTH: 127
<212> TYPE: PRT
<213> ORGANISM: Artificial sequence
<220> FEATURE:
<223> OTHER INFORMATION: synthetic sequence
```

<400> SEQUENCE: 16

Met Arg Val Pro Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Thr Asn Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Ser Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Ile Thr Phe Gly Gln Gly Thr Arg Leu Glu Ile Lys
        115                 120                 125

<210> SEQ ID NO 17
<211> LENGTH: 345
<212> TYPE: DNA
<213> ORGANISM: Artificial sequence
<220> FEATURE:
<223> OTHER INFORMATION: synthetic sequence

<400> SEQUENCE: 17
gaggtccagc tgcaacagtc tggacctgag ctgaagaagc ctgggacttc agtgaggata      60
tcctgcaaga cttctggata cacattcact gaatacacca tccactgggt gaagcagagc    120
catggaaaga gccttgagtg gattggaaac attaatccta caatggtgg tactacctac     180 aaccagaagt tcgaggacaa ggccacattg actgtagaca gtcctccag cacagcctac     240 atggagctcc gcagcctgac atctgaggat tctgcagtct attactgtgc agctggttgg    300
aactttgact actggggcca aggcaccacg ctcaccgtct cctca                    345

<210> SEQ ID NO 18
<211> LENGTH: 321
<212> TYPE: DNA
<213> ORGANISM: Artificial sequence
<220> FEATURE:
<223> OTHER INFORMATION: synthetic sequence

<400> SEQUENCE: 18
gacattgtga tgacccagtc tcacaaattc atgtccacat cagtaggaga cagggtcagc     60
atcatctgca aggccagtca ggatgtgggt actgctgtag actggtatca acagaaacca   120
gggcaatctc ctaaactact gatttactgg gcatccaccc ggcacactgg agtccctgat   180
cgcttcacag gcagtggatc tgggacagat ttcactctca ccatcaccaa tgtgcagtct   240
gaagacctgg cagattattt ctgtcagcaa tataacagct atcctctcac gttcggcgcc   300
gggaccatgc tggatctcaa a                                              321

<210> SEQ ID NO 19
<211> LENGTH: 345
<212> TYPE: DNA
<213> ORGANISM: Artificial sequence
<220> FEATURE:
<223> OTHER INFORMATION: synthetic sequence

<400> SEQUENCE: 19

```
gaggtccaac tggtacagtc tggacctgaa gtgaagaagc tggggctac agtgaagata      60
tcctgcaaga cttctggata cacattcact gaatatacca tacactgggt gaagcaggcc    120
cctggaaagg gccttgagtg gattggaaac atcaatccta acaatggtgg taccacctac   180
aatcagaagt tcgaggacaa ggccacacta actgtagaca agtccaccga tacagcctac    240
atggagctca gcagcctaag atctgaggat actgcagtct attattgtgc agctggttgg    300
aactttgact actggggcca aggaccctg ctcaccgtct cctca                     345
```

<210> SEQ ID NO 20
<211> LENGTH: 321
<212> TYPE: DNA
<213> ORGANISM: Artificial sequence
<220> FEATURE:
<223> OTHER INFORMATION: synthetic sequence

<400> SEQUENCE: 20

```
gacatccaga tgacccagtc tccctcatcc ctgtccacat cagtaggaga cagggtcacc      60
ctcacctgta aggccagtca agatgtgggt actgctgtag actggtatca acagaaacca   120
ggaccatctc ctaaactact gatttattgg gcatccactc ggcacactgg aatccctagt   180
cgcttctcag gcagtggatc tgggacagac ttcactctca ccatttctag tcttcagcct   240
gaagactttg cagattatta ctgtcagcaa tataacagct atcctctcac gttcggtcct   300
gggaccaagg tggacatcaa a                                               321
```

<210> SEQ ID NO 21
<211> LENGTH: 345
<212> TYPE: DNA
<213> ORGANISM: Artificial sequence
<220> FEATURE:
<223> OTHER INFORMATION: synthetic sequence

<400> SEQUENCE: 21

```
gaggtccagc tggtgcagtc tggagctgag gtgaagaagc ctggggcctc agtgaaggtc      60
tcctgcaagg cttctggata cacattcact gaatacacca tccactgggt gaggcaggcc   120
cctggaaagg gccttgagtg gattggaaac attaatccta acaatggtgg tactacctac   180
aaccagaagt tcgaggacag agtcacaatc actgtagaca agtccaccag cacagcctac   240
atggagctca gcagcctgag atctgaggat actgcagtct attactgtgc agcttactgg   300
ctgttcgact actggggcca aggcaccacg gtcaccgtct cctca                    345
```

<210> SEQ ID NO 22
<211> LENGTH: 321
<212> TYPE: DNA
<213> ORGANISM: Artificial sequence
<220> FEATURE:
<223> OTHER INFORMATION: synthetic sequence

<400> SEQUENCE: 22

```
gacattcaga tgacccagtc tcccagcacc ctgtccgcat cagtaggaga cagggtcacc      60
atcacttgca aggccagtca ggatgtgggt actgctgtag actggtatca acagaaacca   120
gggcaagctc ctaaactact gatttactgg gcatccaccc ggcacactgg agtccctgat   180
cgcttcagcg gcagtggatc tgggacagat ttcactctca ccatcagcag actgcagcct   240
gaagactttg cagtttatta ctgtcagcaa tataacagct atcctctcac gttcggccag   300
gggaccaagg tggatatcaa a                                               321
```

<210> SEQ ID NO 23
<211> LENGTH: 345
<212> TYPE: DNA
<213> ORGANISM: Artificial sequence
<220> FEATURE:
<223> OTHER INFORMATION: synthetic sequence

<400> SEQUENCE: 23

```
gaggtccagc tggtgcagtc tggagctgag gtgaagaagc ctggggcctc agtgaaggtc      60
tcctgcaagg cttctggata cacattcact gaatacacca tccactgggt gaggcaggcc     120
cctggaaagg gccttgagtg gattggaaac attaatccta caatggtgg tactacctac      180
aaccagaagt tcgaggacag agtcacaatc actgtagaca gtccaccag cacagcctac      240
atggagctca gcagcctgag atctgaggat actgcagtct attactgtgc aggtgggtgg     300
accttcgact actggggcca aggcaccacg gtcaccgtct cctca                     345
```

<210> SEQ ID NO 24
<211> LENGTH: 321
<212> TYPE: DNA
<213> ORGANISM: Artificial sequence
<220> FEATURE:
<223> OTHER INFORMATION: synthetic sequence

<400> SEQUENCE: 24

```
gacattcaga tgacccagtc tcccagcacc ctgtccgcat cagtaggaga cagggtcacc      60
atcacttgca aggccagtca ggatgtgggt actgctgtag actggtatca acagaaacca     120
gggcaagctc ctaaactact gatttactgg gcatccaccc ggcacactgg agtccctgat     180
cgcttcagcg gcagtggatc tgggacagat ttcactctca ccatcagcag actgcagcct     240
gaagactttg cagtttatta ctgtcagcag ttcaccaggt atcctctcac gttcggccag     300
gggaccaagg tggatatcaa a                                               321
```

<210> SEQ ID NO 25
<211> LENGTH: 345
<212> TYPE: DNA
<213> ORGANISM: Artificial sequence
<220> FEATURE:
<223> OTHER INFORMATION: synthetic sequence

<400> SEQUENCE: 25

```
gaggtccagc tggtgcagtc tggagctgag gtgaagaagc ctggggcctc agtgaaggtc      60
tcctgcaagg cttctggata cacattcact gaatacacca tccactgggt gaggcaggcc     120
cctggaaagg gccttgagtg gattggaaac attaatccta caatggtgg tactacctac      180
aaccagaagt tcgaggacag agtcacaatc actgtagaca gtccaccag cacagcctac      240
atggagctca gcagcctgag atctgaggat actgcagtct attactgtgc aggtgcgtgg     300
accatggact actggggcca aggcaccacg gtcaccgtct cctca                     345
```

<210> SEQ ID NO 26
<211> LENGTH: 321
<212> TYPE: DNA
<213> ORGANISM: Artificial sequence
<220> FEATURE:
<223> OTHER INFORMATION: synthetic sequence

<400> SEQUENCE: 26

```
gacattcaga tgacccagtc tcccagcacc ctgtccgcat cagtaggaga cagggtcacc      60
atcacttgca aggccagtca ggatgtgggt actgctgtag actggtatca acagaaacca     120
```

```
gggcaagctc ctaaactact gatttactgg gcatccaccc ggcacactgg agtccctgat    180
cgcttcagcg gcagtggatc tgggacagat ttcactctca ccatcagcag actgcagcct    240
gaagactttg cagtttatta ctgtcagcaa tataacgcgt actcgttgac gttcggccag    300
gggaccaagg tggatatcaa a                                              321
```

```
<210> SEQ ID NO 27
<211> LENGTH: 345
<212> TYPE: DNA
<213> ORGANISM: Artificial sequence
<220> FEATURE:
<223> OTHER INFORMATION: synthetic sequence

<400> SEQUENCE: 27
```

```
gaggtccagc tggtgcagtc tggagctgag gtgaagaagc ctggggcctc agtgaaggtc     60
tcctgcaagg cttctggata cacattcact gaatacacca tccactgggt gaggcaggcc    120
cctggaaagg gccttgagtg gattggaaac attaatccta acaatggtgg tactacctac    180
aaccagaagt tcgaggacag agtcacaatc actgtagaca agtccaccag cacagcctac    240
atggagctca gcagcccgag atctgaggat actgcagtct attactgtgc agctggttgg    300
aactttgact actggggcca aggcaccacg gtcaccgtct cctca                    345
```

```
<210> SEQ ID NO 28
<211> LENGTH: 345
<212> TYPE: DNA
<213> ORGANISM: Artificial sequence
<220> FEATURE:
<223> OTHER INFORMATION: synthetic sequence

<400> SEQUENCE: 28
```

```
gaggtccagc tggtgcagtc tggagctgag gtgaagaagc ctggggcctc agtgaaggtc     60
tcctgcaagg cttctggata cacattcact gaatacacca tccactgggt gaggcaggcc    120
cctggaaagg gccttgagtg gattggaaac attaatccta acaatggtgg tactacctac    180
aaccagaagt tcgaggacag agtcacaatc actgtagaca agtccaccag cacagcctac    240
atggagctca gcagcctgag atctgaggat actgcagtct attactgtgc agctggttgg    300
aactttgact actggggcca aggcaccacg gtcaccgtct cctca                    345
```

```
<210> SEQ ID NO 29
<211> LENGTH: 115
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (98)..(102)
<223> OTHER INFORMATION: Residues as these positions are selected from
      the following sequences: Ala Tyr Trp Leu Phe, Gly Gly Trp Thr
      Phe, or Gly Ala Trp Thr Met

<400> SEQUENCE: 29
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60
```

-continued

```
Glu Asp Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Xaa Xaa Xaa Xaa Asp Tyr Trp Gly Gln Gly Thr Thr Val Thr
            100                 105                 110

Val Ser Ser
        115

<210> SEQ ID NO 30
<211> LENGTH: 115
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (9)..(9)
<223> OTHER INFORMATION: This residue is selected from Ala or Pro
<220> FEATURE:
<221> NAME/KEY: MISC_FEATURE
<222> LOCATION: (11)..(11)
<223> OTHER INFORMATION: This residue is selected from Val or Leu
<220> FEATURE:
<221> NAME/KEY: MISC_FEATURE
<222> LOCATION: (24)..(24)
<223> OTHER INFORMATION: This residue is selected from Ala or Thr
<220> FEATURE:
<221> NAME/KEY: MISC_FEATURE
<222> LOCATION: (38)..(38)
<223> OTHER INFORMATION: This residue is selected from Arg or Lys
<220> FEATURE:
<221> NAME/KEY: MISC_FEATURE
<222> LOCATION: (41)..(41)
<223> OTHER INFORMATION: This residue is selected from Pro or His
<220> FEATURE:
<221> NAME/KEY: MISC_FEATURE
<222> LOCATION: (55)..(55)
<223> OTHER INFORMATION: This residue is selected from Asn or Gln
<220> FEATURE:
<221> NAME/KEY: MISC_FEATURE
<222> LOCATION: (68)..(68)
<223> OTHER INFORMATION: This residue is selected from Val or Ala
<220> FEATURE:
<221> NAME/KEY: MISC_FEATURE
<222> LOCATION: (70)..(70)
<223> OTHER INFORMATION: This residue is selected from Ile or Leu
<220> FEATURE:
<221> NAME/KEY: MISC_FEATURE
<222> LOCATION: (86)..(86)
<223> OTHER INFORMATION: This residue is selected from Leu or Pro
<220> FEATURE:
<221> NAME/KEY: MISC_FEATURE
<222> LOCATION: (98)..(102)
<223> OTHER INFORMATION: Residues as these positions are selected from
      the following sequences: Ala Tyr Trp Leu Phe, Gly Gly Trp Thr Phe,
      or Gly Ala Trp Thr Met

<400> SEQUENCE: 30

Glu Val Gln Leu Val Gln Ser Gly Xaa Glu Xaa Lys Lys Pro Gly Ala
 1               5                  10                  15

Ser Val Lys Val Ser Cys Lys Xaa Ser Gly Tyr Thr Phe Thr Glu Tyr
                 20                  25                  30

Thr Ile His Trp Val Xaa Gln Ala Xaa Gly Lys Gly Leu Glu Trp Ile
             35                  40                  45

Gly Asn Ile Asn Pro Asn Xaa Gly Gly Thr Thr Tyr Asn Gln Lys Phe
         50                  55                  60

Glu Asp Arg Xaa Thr Xaa Thr Val Asp Lys Ser Thr Ser Thr Ala Tyr
 65                  70                  75                  80
```

```
Met Glu Leu Ser Ser Xaa Arg Ser Glu Asp Thr Ala Val Tyr Tyr Cys
                85                  90                  95

Ala Xaa Xaa Xaa Xaa Xaa Asp Tyr Trp Gly Gln Gly Thr Thr Val Thr
            100                 105                 110

Val Ser Ser
        115

<210> SEQ ID NO 31
<211> LENGTH: 107
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (91)..(95)
<223> OTHER INFORMATION: Residues as these positions are selected from
      the following sequences: Phe Thr Arg Tyr Pro or Tyr Asn Ala Tyr
      Ser

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Xaa Xaa Xaa Xaa Xaa Leu
                85                  90                  95

Thr Phe Gly Gln Gly Thr Lys Val Asp Ile Lys
            100                 105

<210> SEQ ID NO 32
<211> LENGTH: 107
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: This residue is selected from Gln or Val
<220> FEATURE:
<221> NAME/KEY: MISC_FEATURE
<222> LOCATION: (10)..(10)
<223> OTHER INFORMATION: This residue is selected from Thr or Phe
<220> FEATURE:
<221> NAME/KEY: MISC_FEATURE
<222> LOCATION: (63)..(63)
<223> OTHER INFORMATION: This residue is selected from Ser or Thr
<220> FEATURE:
<221> NAME/KEY: MISC_FEATURE
<222> LOCATION: (80)..(80)
<223> OTHER INFORMATION: This residue is selected from Pro or Ser
<220> FEATURE:
<221> NAME/KEY: MISC_FEATURE
<222> LOCATION: (85)..(85)
<223> OTHER INFORMATION: This residue is selected from Val or Asp
<220> FEATURE:
<221> NAME/KEY: MISC_FEATURE
<222> LOCATION: (87)..(87)
<223> OTHER INFORMATION: This residue is selected from Tyr or Phe
```

```
<220> FEATURE:
<221> NAME/KEY: MISC_FEATURE
<222> LOCATION: (91)..(95)
<223> OTHER INFORMATION: Residues as these positions are selected from
      the following sequences: Phe Thr Arg Tyr Pro or Tyr Asn Ala Tyr
      Ser
<220> FEATURE:
<221> NAME/KEY: MISC_FEATURE
<222> LOCATION: (103)..(103)
<223> OTHER INFORMATION: This residue is selected from Lys or Met

<400> SEQUENCE: 32

Asp Ile Xaa Met Thr Gln Ser Pro Ser Xaa Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Xaa Gly
    50                  55                  60

Ser Gly Ser Gly Thr Asp Phe Thr Leu Thr Ile Ser Arg Leu Gln Xaa
65                  70                  75                  80

Glu Asp Phe Ala Xaa Tyr Xaa Cys Gln Gln Xaa Xaa Xaa Xaa Xaa Leu
                85                  90                  95

Thr Phe Gly Gln Gly Thr Xaa Val Asp Ile Lys
                100                 105

<210> SEQ ID NO 33
<211> LENGTH: 5
<212> TYPE: PRT
<213> ORGANISM: Artificial sequence
<220> FEATURE:
<223> OTHER INFORMATION: synthetic sequence

<400> SEQUENCE: 33

Glu Tyr Thr Ile His
1               5

<210> SEQ ID NO 34
<211> LENGTH: 17
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (6)..(6)
<223> OTHER INFORMATION: This residue is selected from Asn or Gln

<400> SEQUENCE: 34

Asn Ile Asn Pro Asn Xaa Gly Gly Thr Thr Tyr Asn Gln Lys Phe Glu
1               5                   10                  15

Asp

<210> SEQ ID NO 35
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(4)
<223> OTHER INFORMATION: Residues as these positions are selected from
      the following sequences: Tyr Trp Leu Phe, Gly Trp Thr Phe or Ala
      Tyr Thr Met
```

```
<400> SEQUENCE: 35

Xaa Xaa Xaa Xaa Asp Tyr
1               5

<210> SEQ ID NO 36
<211> LENGTH: 11
<212> TYPE: PRT
<213> ORGANISM: Artificial sequence
<220> FEATURE:
<223> OTHER INFORMATION: synthetic sequence

<400> SEQUENCE: 36

Lys Ala Ser Gln Asp Val Gly Thr Ala Val Asp
1               5                   10

<210> SEQ ID NO 37
<211> LENGTH: 7
<212> TYPE: PRT
<213> ORGANISM: Artificial sequence
<220> FEATURE:
<223> OTHER INFORMATION: synthetic sequence

<400> SEQUENCE: 37

Trp Ala Ser Thr Arg His Thr
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (3)..(7)
<223> OTHER INFORMATION: Residues as these positions are selected from
      the following sequences: Phe Thr Arg Tyr Pro or Tyr Asn Ala Tyr
      Ser

<400> SEQUENCE: 38

Gln Gln Xaa Xaa Xaa Xaa Xaa Leu Thr
1               5

<210> SEQ ID NO 39
<211> LENGTH: 4
<212> TYPE: PRT
<213> ORGANISM: Artificial sequence
<220> FEATURE:
<223> OTHER INFORMATION: synthetic sequences

<400> SEQUENCE: 39

Tyr Trp Leu Phe
1

<210> SEQ ID NO 40
<211> LENGTH: 4
<212> TYPE: PRT
<213> ORGANISM: Artificial sequence
<220> FEATURE:
<223> OTHER INFORMATION: synthetic sequences

<400> SEQUENCE: 40

Gly Trp Thr Phe
1
```

```
<210> SEQ ID NO 41
<211> LENGTH: 4
<212> TYPE: PRT
<213> ORGANISM: Artificial sequence
<220> FEATURE:
<223> OTHER INFORMATION: synthetic sequences

<400> SEQUENCE: 41

Ala Trp Thr Met
1

<210> SEQ ID NO 42
<211> LENGTH: 5
<212> TYPE: PRT
<213> ORGANISM: Artificial sequence
<220> FEATURE:
<223> OTHER INFORMATION: synthetic sequences

<400> SEQUENCE: 42

Ala Tyr Trp Leu Phe
1               5

<210> SEQ ID NO 43
<211> LENGTH: 5
<212> TYPE: PRT
<213> ORGANISM: Artificial sequence
<220> FEATURE:
<223> OTHER INFORMATION: synthetic sequences

<400> SEQUENCE: 43

Gly Gly Trp Thr Phe
1               5

<210> SEQ ID NO 44
<211> LENGTH: 5
<212> TYPE: PRT
<213> ORGANISM: Artificial sequence
<220> FEATURE:
<223> OTHER INFORMATION: synthetic sequences

<400> SEQUENCE: 44

Gly Ala Trp Thr Met
1               5

<210> SEQ ID NO 45
<211> LENGTH: 5
<212> TYPE: PRT
<213> ORGANISM: Artificial sequence
<220> FEATURE:
<223> OTHER INFORMATION: synthetic sequences

<400> SEQUENCE: 45

Phe Thr Arg Tyr Pro
1               5

<210> SEQ ID NO 46
<211> LENGTH: 5
<212> TYPE: PRT
<213> ORGANISM: Artificial sequence
<220> FEATURE:
<223> OTHER INFORMATION: synthetic sequences

<400> SEQUENCE: 46

Tyr Asn Ala Tyr Ser
1               5
```